(12) United States Patent
Schreiber et al.

(10) Patent No.: US 10,391,154 B2
(45) Date of Patent: Aug. 27, 2019

(54) COMPOSITIONS AND METHODS FOR TREATING OR AMELIORATING FIBROSIS, SYSTEMIC SCLEROSIS AND SCLERODERMA

(71) Applicant: LEADIANT BIOSCIENCES LTD., London (GB)

(72) Inventors: Brian Dean Schreiber, Oshkosh, WI (US); Gianfranco Fornasini, Bethesda, MD (US); Nadejda Soukhareva, Derwood, MD (US); Santosh Kumar Ramamurthy, Columbia, MD (US)

(73) Assignee: LEADIANT BIOSCIENCES LTD., London (GB)

( * ) Notice: Subject to any disclaimer, the term of this patent is extended or adjusted under 35 U.S.C. 154(b) by 0 days.

(21) Appl. No.: 16/037,795

(22) Filed: Jul. 17, 2018

(65) Prior Publication Data

US 2019/0022196 A1    Jan. 24, 2019

Related U.S. Application Data

(60) Provisional application No. 62/534,468, filed on Jul. 19, 2017.

(51) Int. Cl.
| | |
|---|---|
| *A61K 38/50* | (2006.01) |
| *A61K 47/60* | (2017.01) |
| *A61P 9/10* | (2006.01) |
| *C07K 14/47* | (2006.01) |
| *A61K 45/06* | (2006.01) |

(52) U.S. Cl.
CPC .............. *A61K 38/50* (2013.01); *A61K 47/60* (2017.08); *A61P 9/10* (2018.01); *C07K 14/47* (2013.01); *A61K 45/06* (2013.01); *C12Y 305/04004* (2013.01)

(58) Field of Classification Search
None
See application file for complete search history.

(56) References Cited

U.S. PATENT DOCUMENTS

| | | | |
|---|---|---|---|
| 5,728,560 | A | 3/1998 | Shorr et al. |
| 8,071,741 | B2 | 12/2011 | Filpula et al. |
| 2008/0159964 | A1 | 7/2008 | Blackburn et al. |

FOREIGN PATENT DOCUMENTS

WO    2008131208 A1    10/2008

OTHER PUBLICATIONS

Fernandez et al. "Pharmacological Blockade of A2A Receptors Prevents Dermal Fibrosis in a Model of Elevated Tissue Adenosine" The American Journal of Pathology, vol. 172, No. 6, Jun. 2008 (Year: 2008).*
Blackburn et al. "The Use of Enzyme Therapy to Regulate the Metabolic and Phenotypic Consequences of Adenosine Deaminase Deficiency in Mice" The Journal of Biological Chemistry vol. 275, No. 41, Issue of Oct. 13, pp. 32114-32121, 2000 (Year: 2000).*
Xu et al., Absence of the adenosine A2a receptor confers pulmonary arterial hypertension and increased pulmonary vascular remodeling in mice: Journal of Vascular Research, 2011, v 48, p. 171-183.
Liu et al., "Beneficial and detrimental role of adenosine signaling in diseases and therapy" J. Appl. Physiol, 2015, v 119, p. 1173-1182.
Foral, International Search Report and Written Opinion for PCT/EP2018/069447, dated Sep. 26, 2018.
Sasaki et al. "Serum adenosine deaminase activity in systemic sclerosis (scleroderma) and related disorders" Journal of American Academy of Dermatology, Sep. 1992, v 27, n 3, p. 411-414.
Meunier et al., "Adenosine Deaminase in Progressive Systemic Sclerosis" Acta Derm Venereol, 1995, v 75, p. 297-299.
Fernandez et al. "Extracellular Generation of Adenosine by the Ectonucleotidases CD39 and CD73 Promotes Dermal Fibrosis" The American Journal of Pathology, Dec. 2013, v 183, n 6, p. 1740-1746.
Fernandez et al., "Pharmacological Blockade of A2A Receptors Prevents Dermal Fibrosis in a Model of Elevated Tissue Adenosine" The American Journal of Pathology, Jun. 2008, v 172, n 6, p. 1675-1682.
Chunn et al., "Partially adenosine deaminase-deficient mice develop pulmonary fibrosis in association with adenosine elevations" Am J Physiol Lung Cell Mol Physiol, Mar. 2006, v 290, p. L579-L587.
Chunn et al., "Adenosine-Dependent Pulmonary Fibrosis in Adenosine Deaminase-Deficient Mice" J Immunol, 2005, v 175, p. 1937-1946.
Chan et al., "Adenosine A2A Receptors in Diffuse Dermal Fibrosis" Arthritis and Rheumatism, Aug. 2006, v 54, n 8, p. 2632-2642.
Blackburn et al., "Adenosine mediates IL-13—induced inflammation and remodeling in the lung and interacts in an IL-13—adenosine amplification pathway" The Journal of Clinical Investigation, Aug. 2003, v 112, n 3, p. 332-344.
Asano et al., "Vasculopathy in scleroderma" Semin Immunopathol, Jul. 8, 2015.

* cited by examiner

*Primary Examiner* — Thane Underdahl
(74) *Attorney, Agent, or Firm* — Greer, Burns & Crain, Ltd.; Gregory P. Einhorn

(57) ABSTRACT

Provided are Adenosine Deaminase (ADA), or a polypeptides or peptides having an ADA activity, or an ADA conjugate, pharmaceutical compositions and formulations, products of manufacture and kits, and methods containing them for the prevention and treatment of a scleroderma-associated vasculopathy, in particular proliferative obliterative vasculopathy, progressive obliterative vasculopathy or an idiopathic obliterative vasculopathy and/or preventing or decreasing the progression of scleroderma, wherein optionally the scleroderma comprises a local scleroderma or a diffuse, or a systemic scleroderma.

20 Claims, 3 Drawing Sheets

Specification includes a Sequence Listing.

COMPOSITIONS AND METHODS FOR TREATING OR AMELIORATING FIBROSIS, SYSTEMIC SCLEROSIS AND SCLERODERMA

RELATED APPLICATIONS

This Patent Convention Treaty (PCT) International Application claims the benefit of priority to U.S. Provisional Application Ser. No. 62/534,468, filed Jul. 19, 2017. The aforementioned application is expressly incorporated herein by reference in its entirety and for all purposes.

TECHNICAL FIELD

This invention generally relates to the prevention and treatment of a scleroderma-associated vasculopathy. In alternative embodiments, provided are pharmaceutical compositions and formulations, products of manufacture and kits, and methods for using them, for: the prevention and treatment of scleroderma-associated vasculopathies and vascular changes, in particular a proliferative obliterative vasculopathy such as idiopathic obliterative vasculopathy and progressive obliterative vasculopathy, causing structural and functional abnormalities such as Raynaud's syndrome (also called "Raynaud's phenomenon (RP)"), edematous puffy hands, telangiectasias, digital ulcers, pulmonary arterial hypertension (PAH), myocardial dysfunction, and scleroderma renal crisis. In alternative embodiments, provided are an Adenosine Deaminase (ADA), or the polypeptide or peptide having ADA activity, including ADA conjugates, for use in treating, ameliorating or preventing: scleroderma-associated vasculopathies and vascular changes, in particular a proliferative obliterative vasculopathy such as idiopathic obliterative vasculopathy and progressive obliterative vasculopathy, causing structural and functional abnormalities such as Raynaud's syndrome, edematous puffy hands, telangiectasias, digital ulcers, pulmonary arterial hypertension (PAH), myocardial dysfunction, and scleroderma renal crisis. In alternative embodiments, provided are an Adenosine Deaminase (ADA), or the polypeptide or peptide having ADA activity, including ADA conjugates, for use in preventing or decreasing the progression of scleroderma, wherein optionally the scleroderma comprises a local scleroderma or a diffuse, or a systemic scleroderma.

BACKGROUND

Systemic sclerosis (SSc) is a multisystem connective tissue disorder featured by vascular injury as well as fibrosis of the skin and various internal organs with an autoimmune background. Although the pathogenesis of SSc still remains elusive, it is generally accepted that initial vascular injury due to autoimmunity and environmental factors causes structural and functional abnormalities of the vasculature which eventually result in the constitutive activation of fibroblasts and their evolution to myofibroblasts in various organs.

SSc is characterized by structural alteration of the vasculature, which includes destructive vasculopathy, or loss of small vessels and progressive obliterative vasculopathy, thickening of vessel walls and occlusion of arterioles and small arteries. SSc also is characterized by impaired vasculogenesis and angiogenesis.

Impaired function of SSC vasculature includes the altered expression of cell adhesion molecules, endothelial dysfunction, activated endothelial to mesenchymal transition leading to abnormalities of the vasculature and impaired coagulation/thrombosis.

Structural abnormalities of the vasculature in SSc patients are classified into two categories, these being destructive vasculopathy and proliferative obliterative vasculopathy. Destructive vasculopathy is characterized by a progressive loss of small blood vessels, whereas proliferative obliterative vasculopathy is due to excessive proliferation of vascular endothelial and smooth muscle cells leading to the occlusion of arterioles and small arteries. The vascular abnormalities are caused by impaired or abnormal compensatory vasculogenesis, along with angiogenesis, and vascular remodeling, which leads to tissue hypoxia and dermal fibroblast activation, and other features of scleroderma such as digital ulcers, PAH, and scleroderma renal crisis.

SUMMARY

In alternative embodiments, provided are an Adenosine Deaminase (ADA), or the polypeptide or peptide having ADA activity, including ADA conjugates, for use in arresting, treating, ameliorating or preventing or decreasing the progression of:

(i) a scleroderma-associated vasculopathy and vascular changes, in particular, a proliferative obliterative vasculopathy, such as idiopathic obliterative vasculopathy and progressive obliterative vasculopathy, Raynaud's syndrome, edematous puffy hands, telangiectasias, digital ulcers, pulmonary arterial hypertension (PAH), myocardial dysfunction, and scleroderma renal crisis;

(ii) vascular wall thickening in a scleroderma patient, wherein optionally the scleroderma comprises a local scleroderma or a diffuse, or a systemic scleroderma, and optionally systemic sclerosis, a scleroderma-associated vasculopathy or a scleroderma-associated obliterative vasculopathy, wherein optionally the proliferative obliterative vasculopathy is an idiopathic obliterative vasculopathy or a progressive obliterative vasculopathy;

(iii) vascular occlusion in a scleroderma patient, wherein optionally the scleroderma comprises a local scleroderma or a diffuse, or a systemic scleroderma, or in an individual with a scleroderma-associated vasculopathy or a proliferative obliterative vasculopathy, optionally an idiopathic obliterative vasculopathy or a progressive obliterative vasculopathy, associated with systemic sclerosis (iv) Raynaud's syndrome associated with scleroderma, nonpitting edema of the hands, distal finger ulcers and/or facial or peri-oral skin tightening with decreased oral aperture, wherein the Raynaud's syndrome, nonpitting edema of the hands, distal finger ulcers and/or facial or peri-oral skin tightening are early pathological expressions of scleroderma.

Also disclosed are methods for arresting, treating, ameliorating or preventing or decreasing the progression of the above-mentioned diseases or conditions comprising:

(a) administering to the individual in need thereof an effective amount of an agent, a compound or a composition having an Adenosine Deaminase enzyme (also known as adenosine aminohydrolase, or ADA) activity, or is capable of increasing or sustaining levels of ADA activity in the individual, or (b) (1) providing an effective amount of an agent, a compound or a composition having an Adenosine Deaminase enzyme (also known as adenosine aminohydrolase, or ADA) activity, or is capable of increasing or sustaining levels of ADA activity in the individual, and (2) administering the agent, compound or composition to the individual in need thereof, thereby (i) arresting, treating, ameliorating or preventing or decreasing the progression of: a scleroderma-associated vasculopathy, optionally a scleroderma-associated proliferative obliterative vasculopathy, optionally an idiopathic obliterative vasculopathy or a progressive obliterative vasculopathy, in an individual in need thereof;

(ii) arresting, treating, ameliorating or preventing or decreasing the progression of vascular wall thickening in a scleroderma patient, wherein optionally the scleroderma comprises a local scleroderma or a diffuse, or a systemic scleroderma, and optionally the arresting, treating, ameliorating or preventing or decreasing the progression of systemic sclerosis, a scleroderma-associated vasculopathy or a proliferative obliterative vasculopathy, wherein optionally the proliferative obliterative vasculopathy is an idiopathic obliterative vasculopathy or a progressive obliterative vasculopathy (iii) arresting, treating, ameliorating or preventing or decreasing the progression of vascular vessel occlusion in a scleroderma patient, wherein optionally the scleroderma comprises a local scleroderma or a diffuse, or a systemic scleroderma, or in an individual with a scleroderma-associated vasculopathy or a proliferative obliterative vasculopathy, optionally an idiopathic obliterative vasculopathy or a progressive obliterative vasculopathy associated with systemic sclerosis;

(iv) arresting, treating, ameliorating or preventing or decreasing the progression of Raynaud's syndrome associated with scleroderma, nonpitting edema of the hands, distal finger ulcers and/or facial and/or peri-oral skin tightening with decreased oral aperture, wherein the Raynaud's syndrome, nonpitting edema of the hands, distal finger ulcers and/or facial or peri-oral skin tightening are early pathological expressions of scleroderma;

(v) preventing or decreasing the progression of scleroderma, wherein optionally the scleroderma comprises a local scleroderma or a diffuse, or a systemic scleroderma.

In alternative embodiments, provided are methods wherein the agent, compound or composition comprises or is an Adenosine Deaminase enzyme (also known as adenosine aminohydrolase, or ADA) or a polypeptide or peptide having Adenosine Deaminase activity.

In alternative embodiments, provided are an agent, compound or composition comprising or being an Adenosine Deaminase enzyme (also known as adenosine aminohydrolase, or ADA) or a polypeptide or peptide having Adenosine Deaminase activity for use in arresting, treating, ameliorating or preventing any of the above listed diseases, more in particular:

(i) a scleroderma-associated vasculopathy, optionally a scleroderma-associated proliferative obliterative vasculopathy, optionally an idiopathic obliterative vasculopathy or a progressive obliterative vasculopathy;

(ii) vascular wall thickening in a scleroderma patient, wherein optionally the scleroderma comprises a local scleroderma or a diffuse, or a systemic scleroderma, and optionally the arresting, treating, ameliorating or preventing in an individual with focal or localized or systemic sclerosis, a scleroderma-associated vasculopathy or a proliferative obliterative vasculopathy, wherein optionally the proliferative obliterative vasculopathy is an idiopathic obliterative vasculopathy or a progressive obliterative vasculopathy:

(iii) vascular vessel occlusion in a scleroderma patient, wherein optionally the scleroderma comprises a local scleroderma or a diffuse, or a systemic scleroderma, a scleroderma-associated vasculopathy or a proliferative obliterative vasculopathy, optionally an idiopathic obliterative vasculopathy or a progressive obliterative vasculopathy associated with systemic sclerosis;

(iv) Raynaud's syndrome associated with scleroderma, nonpitting edema of the hands, distal finger ulcers and/or facial or peri-oral skin tightening with decreased oral aperture, wherein the Raynaud's syndrome, nonpitting edema of the hands, distal finger ulcers and/or facial or peri-oral skin tightening are early pathological expressions of scleroderma;

(v) preventing or decreasing the progression of scleroderma, wherein optionally the scleroderma comprises a local scleroderma or a diffuse, or a systemic scleroderma; and/or (vi) wherein the agent, compound or composition is used as a supplementary treatment to any of the above listed diseases or conditions, or the agent, compound or composition is administered to patients who have failed other scleroderma treatments.

In alternative embodiments, provided are methods wherein the agent, compound or composition is or comprises: a recombinant, an isolated, an extracted, a synthetic or a peptidomimetic version of the agent, compound or composition having an Adenosine Deaminase enzyme (also known as adenosine aminohydrolase, or ADA) activity, or is capable of increasing or sustaining levels of ADA activity in the individual, or the polypeptide or peptide having Adenosine Deaminase activity.

In alternative embodiments, the individual is a mammal, or a human.

In alternative embodiments, the Adenosine Deaminase (ADA), or the polypeptide or peptide having Adenosine Deaminase activity, is or is derived from a human or other mammalian source, optionally a bovine source or a source as described in U.S. Pat. No. 8,071,741, or a mixture thereof.

In alternative embodiments, provided are the Adenosine Deaminase (ADA), or the polypeptide or peptide having Adenosine Deaminase (ADA) activity is:

(a) manufactured as or is formulated in a polyethylene glycol conjugate form, or is administered in a polyethylene glycol conjugate form, wherein optionally the polyethylene glycol conjugate form is a PEGylated bovine adenosine deaminase enzyme, which optionally comprises a (monomethoxypolyethylene glycol succinimidyl) 11-17-adenosine deaminase (CAS 130167-68-9), also named pegademase bovine, also known as ADAGEN® (Leadiant Biosciences Ltd., Windsor, UK); or in alternative embodiment is a poly(oxy-1,2-ethanediyl), α-carboxy-ω-methoxy-, amide with an ADA (also named elapegademase—CAS 1709806-75-6- or EZN2279) or in alternative embodiment a polypeptide having ADA activity, or (b) conjugated to, linked to or covalently linked to a non-antigenic polymer, gelatin, or nanoparticles or other release system known by practitioners of the art, wherein optionally the non-antigenic polymer comprises a polyalkylene oxide.

In alternative embodiments, the agent, compound or composition is formulated as a pharmaceutical composition, or is formulated for administration in vivo; or formulated for enteral or parenteral administration, or for oral, topical, subcutaneous, intramuscular (IM), intravenous (IV) or intrathecal (IT) administration, or by inhalation or spray, wherein optionally the compound or formulation is administered orally, parenterally, by inhalation spray, nasally, topically, intrathecally, intracerebrally, epidurally, intracranially or rectally;

wherein optionally the formulation or pharmaceutical composition is contained in or carried in a nanoparticle, a particle, a micelle or a liposome or lipoplex, a polymersome, a polyplex or a dendrimer; or wherein optionally the compound or composition, or the formulation or pharmaceutical composition, is formulated as, or contained in, a nanoparticle, a liposome, a tablet, a pill, a capsule, a gel, a geltab, a liquid, a powder, an emulsion, a lotion, an aerosol, a spray, a lozenge, an aqueous or a sterile or an injectable solution, or an implant.

In alternative embodiments, an effective amount of Adenosine Deaminase (ADA), or the polypeptide or peptide having ADA activity, administered to an individual in need thereof is:

(a) from about 0.01 to about 100 mg/kg, for example from about 1 to about 100 mg/kg, or from about 5 to about 50 mg/kg, or from about 10 to about 30 mg/kg subdivided into multiple administrations from a minimum of once a day to once a year;

(b) from about 5 U/kg to about 50 U/kg, for example from about 10 U/kg to about 30 U/kg, or from about 20 U/kg to about 60 U/kg, or from about 0.5 U/kg to about 5 U/kg (e.g., about 1 U/kg), supraphysiological doses can also be provided, for example up to 100 U/kg;

(c) about 250 units/ml administered weekly, optionally administered subcutaneously or IM; or (d) any of (a) to (c), wherein the dosage is individualized based on monitoring of plasma ADA activity, adenosine levels and/or other specific biomarkers after initial administrations.

In alternative embodiments, an effective amount of Adenosine Deaminase (ADA), or the polypeptide or peptide having ADA activity, administered to an individual in need thereof comprises use of various dosing schedules, optionally using:

a dosing schedule of about 10 U/kg, or between about 5 to 15 U/kg, Adagen (or about 0.067 mg/kg, or between about 0.001 to 0.12 mg/kg, for example 0.03 to 0.12 mg/kg, EZN2279) for the first dose;

about 15 U/kg, or between about 5 to 15 U/kg, Adagen (or about 0.1 mg/kg or between about 0.05 to 0.5 mg/kg, EZN2279) for the second dose, and/or about 30 U/kg Adagen, for example 20 U/kg or between about 15 to 25 or 30 U/kg, (or about 0.134 mg/kg, or between about 0.05 to 0.30, for example 0.25 mg/kg, EZN2279) for the third dose; if necessary or desired, supraphysiological doses may also be foreseen, for example up to 100 U/kg.

In alternative embodiments, provided are kits comprising a compound or composition or a formulation or a pharmaceutical composition as provided herein, and optionally comprising instructions on practicing a method as provided herein.

In alternative embodiments, provided are uses of a compound or composition or a formulation as provided herein, in the manufacture of a medicament.

Use of a compound or composition, or a formulation or a pharmaceutical composition as provided herein in the manufacture of a medicament for:

(i) arresting, treating, ameliorating or preventing: scleroderma-associated vasculopathies, optionally a scleroderma-associated proliferative obliterative vasculopathy, optionally an idiopathic obliterative vasculopathy or a progressive obliterative vasculopathy, in an individual in need thereof;

(ii) arresting, treating, ameliorating or preventing vascular wall thickening in a scleroderma patient, wherein optionally the scleroderma comprises a local or focal scleroderma or a diffuse, or a systemic scleroderma, and optionally the arresting, treating, ameliorating or preventing in an individual with a local or focal, or systemic, sclerosis, a scleroderma-associated vasculopathy or a proliferative obliterative vasculopathy, wherein optionally the proliferative obliterative vasculopathy is an idiopathic obliterative vasculopathy or a progressive obliterative vasculopathy (iii) arresting, treating, ameliorating or preventing vascular vessel occlusion in a scleroderma patient, wherein optionally the scleroderma comprises a local or focal scleroderma or a diffuse, or a systemic scleroderma, or in an individual with a scleroderma-associated vasculopathy or a proliferative obliterative vasculopathy, optionally an idiopathic obliterative vasculopathy or a progressive obliterative vasculopathy associated with systemic sclerosis;

(iv) arresting, treating, ameliorating or preventing Raynaud's syndrome associated with scleroderma, nonpitting edema of the hands, distal finger ulcers and/or facial or peri-oral skin tightening with decreased oral aperture, wherein the Raynaud's syndrome, nonpitting edema of the hands, distal finger ulcers and/or facial or peri-oral skin tightening are early pathological expressions of scleroderma;

(v) preventing or decreasing the progression of scleroderma, wherein optionally the scleroderma comprises a local or focal scleroderma or a diffuse, or a systemic scleroderma.

In alternative embodiments, provided are compounds or compositions or formulations as provided herein, for use in:

(i) arresting, treating, ameliorating or preventing: scleroderma-associated vasculopathies, optionally a scleroderma-associated proliferative obliterative vasculopathy, optionally an idiopathic obliterative vasculopathy or a progressive obliterative vasculopathy, in an individual in need thereof;

(ii) arresting, treating, ameliorating or preventing vascular wall thickening in a scleroderma patient, wherein optionally the scleroderma comprises a local or focal scleroderma or a diffuse, or a systemic scleroderma, and optionally the arresting, treating, ameliorating or preventing in an individual with or a systemic sclerosis, a scleroderma-associated vasculopathy or a proliferative obliterative vasculopathy, wherein optionally the obliterative vasculopathy is an idiopathic obliterative vasculopathy or a progressive obliterative vasculopathy (iii) arresting, treating, ameliorating or preventing vascular vessel occlusion in a scleroderma patient, wherein optionally the scleroderma comprises a local or focal scleroderma or a diffuse, or a systemic scleroderma, or in an individual with a scleroderma-associated vasculopathy or an obliterative vasculopathy, optionally an idiopathic obliterative vasculopathy or a progressive proliferative obliterative vasculopathy associated with systemic sclerosis;

(iv) arresting, treating, ameliorating or preventing Raynaud's syndrome associated with scleroderma, nonpitting edema of the hands, distal finger ulcers, and/or facial or peri-oral skin tightening with decreased oral aperture, wherein the Raynaud's syndrome, nonpitting edema of the hands, distal finger ulcers and/or facial or peri-oral skin tightening are early pathological expressions of scleroderma;

(v) preventing or decreasing the progression of scleroderma, wherein optionally the scleroderma comprises a local or focal scleroderma or a diffuse, or a systemic scleroderma;
wherein optionally the use comprises a method for administering to an individual in need thereof,
wherein the individual in need thereof has or is developing or is predisposed to:
(i) a scleroderma-associated vasculopathy, optionally a proliferative obliterative vasculopathy, optionally an idiopathic obliterative vasculopathy or a progressive obliterative vasculopathy;
(ii) a vascular wall thickening caused by a scleroderma, wherein optionally the scleroderma comprises a local or focal scleroderma or a diffuse, or a systemic scleroderma;
(iii) a vascular vessel occlusion caused by a scleroderma, wherein optionally the scleroderma comprises a local or focal scleroderma or a diffuse, or a systemic scleroderma, or a scleroderma-associated vasculopathy or a scleroderma-associated proliferative obliterative vasculopathy, optionally an idiopathic obliterative vasculopathy or a progressive obliterative vasculopathy, or a systemic sclerosis or
(iv) the individual in need thereof has or is developing or is predisposed to a systemic sclerosis, or Raynaud's syndrome associated with scleroderma, nonpitting edema of the hands, distal finger ulcers and/or facial or peri-oral skin tightening with decreased oral aperture; and/or
(v) the individual in need thereof has or is developing or is predisposed to is developing a scleroderma, wherein optionally the scleroderma comprises a local or focal scleroderma or a diffuse, or a systemic scleroderma;

The details of one or more exemplary embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

DESCRIPTION OF DRAWINGS

The drawings set forth herein are illustrative of exemplary embodiments provided herein and are not meant to limit the scope of the invention as encompassed by the claims.

Figures are described in detail herein.

Like reference symbols in the various drawings indicate like elements.

DETAILED DESCRIPTION

Figure 1:
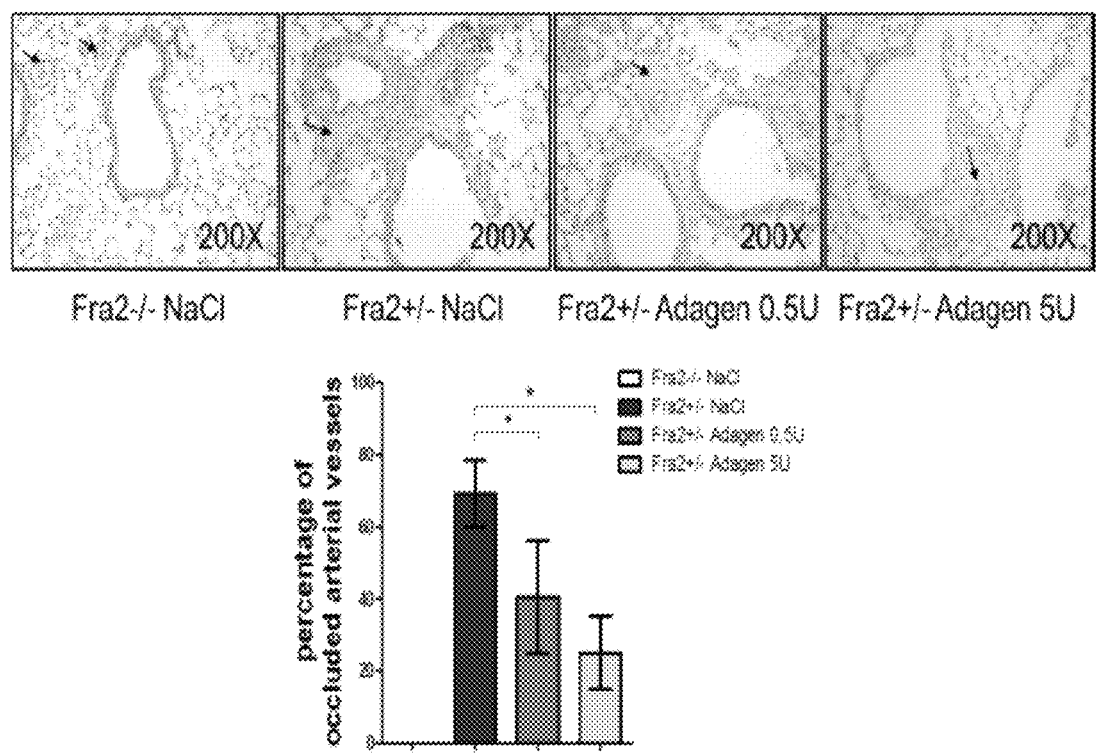
FIG. 1 illustrates images of data, and graphically illustrates data, from experiments where ADAGEN® pegylated adenosine deaminase (Leadiant Biosciences Ltd., Windsor, UK) significantly reduced the number of occluded pulmonary vessels in Fra2 transgenic (tg) mice with decreases from 69.2+/−20.5% in vehicle treated Fra2 tg mice to 40.6+/−15.7% and 25+/−20.4% in Fra2 tg mice treated with ADAGEN® in doses of 0.5 and 5 U respectively. The differences between both dosage levels of ADAGEN® and vehicle in regard to vessel occlusion were both significant with $P<0.05$.

In alternative embodiments, provided are pharmaceutical compositions and formulations, products of manufacture and kits, and methods for using them, for treating, ameliorating, reversing, or abating or diminishing the symptoms of, or preventing scleroderma-associated vasculopathies, optionally a vasculopathy associated with scleroderma; a scleroderma-associated proliferative obliterative vasculopathy such as idiopathic obliterative vasculopathy or progressive obliterative vasculopathy.

In alternative embodiments, provided are an Adenosine Deaminase (ADA), or a polypeptide or a peptide having ADA activity, including ADA conjugates for use in treating, ameliorating or preventing scleroderma-associated vasculopathies and vascular changes, in particular a progressive obliterative vasculopathy such as idiopathic obliterative vasculopathy and progressive obliterative vasculopathy, Raynaud's syndrome, edematous puffy hands, telangiectasias, digital ulcers, pulmonary arterial hypertension (PAH), myocardial dysfunction, and scleroderma renal crisis.

In alternative embodiments, provided are methods for administering an effective amount of an Adenosine Deaminase (ADA), or a polypeptide or a peptide having ADA activity, including ADA conjugates to an individual in need thereof to treat, ameliorate or prevent scleroderma-associated vasculopathies; in particular scleroderma-associated vasculopathies and vascular changes, in particular a proliferative obliterative vasculopathy such as idiopathic obliterative vasculopathy and progressive obliterative vasculopathy, Raynaud's syndrome, edematous puffy hands, telangiectasias, digital ulcers, pulmonary arterial hypertension (PAH), myocardial dysfunction, and scleroderma renal crisis.

In alternative embodiments, provided are methods for administering an effective amount of an Adenosine Deaminase (ADA), or a polypeptide or a peptide having ADA activity, including ADA conjugates to an individual in need thereof to prevent or decrease the progression of scleroderma.

Described herein is an in vivo study using an art-accepted SSc animal model, the Fra2 mouse model of SSc (see e.g., Maurer et al, Vascul Pharmacol. (2013) March; 58(3):194-201; Beyer et al., Arthritis & Rheumatology, October 2010, 62(10):2831-2844). The Fra2 (Fos-related antigen-2) transgenic mouse is a model of scleroderma that incorporates both the vascular and fibrotic features of scleroderma, vascular changes being first detectable by the age of nine weeks and precede the onset of fibrosis thereby imitating the pathology of systemic sclerosis. The Fra2 mouse eventually develops pulmonary disease and dies of respiratory failure anywhere in the range of 18-22 weeks. In these experiments, treatment of the Fra2 mice began at eight weeks and the mice were sacrificed and tissue samples studied at 16 weeks of age. Four groups of mice were studied in this experiment.

Group 1) Wild type control mice treated with the vehicle for ADA

Group 2) Fra2 transgenic mice treated only with the vehicle for ADA

Group 3) (treatment group 1) Fra2 TG mice treated with low dose ADA (0.5 U/week (wk) i.p.)

Group 4) Group 4 (treatment group 2) Fra2 TG mice treated with high dose ADA (5 U 1×/week i.p.)

Outcome Measures:

Histological evaluation of vascular remodeling in pulmonary arteries; vessel wall thickness of the pulmonary arteries was assessed by measuring the thickness of SM22-positive vessel walls with an average vessel wall diameter greater than (>) 10% of normal considered to represent pathology. Three measurements were taken to determine the thickness of each wall. In addition, the degree of luminal occlusion of pulmonary arteries was determined by a manual count of arteries with occluded luminae;

The data clearly illustrate that ADA administration to this SSc model profoundly affected vascular wall thickness. In the control, non-treated Fra2 mouse, the mean thickness of the vessel wall of pulmonary arteries was increased by 1.81+/−0.31 fold compared to non-Fra2 transgenic control mice. Treatment with ADA was associated with significantly decreased thickening of the vessel walls of the pulmonary arteries, reducing the relative vessel wall thickness to 1.21+/−0.19 in Fra2 mice given 0.5 units of ADA and to 1.09+/−0.04 fold when given 5 units of ADA. This improvement in vascular thickening demonstrates the in vivo efficacy of ADA administration for the prevention or decrease of the progression of SSc and related disorders, particularly the vascular component of the pathology of SSc, which has not been addressed by previous anti-inflammatory or anti-thrombotic therapies or other therapies for scleroderma.

Another prominent aspect of the vasculopathy that is an important aspect of local or focal or systemic scleroderma is occlusion of arteries due to the combined pathophysiology of SSc vessels described above. In experiments treating the transgenic (tg) Fra2 mice, it was demonstrated that ADA significantly reduced the number of occluded pulmonary vessels in Fra2 tg mice with decreases from 69.2+/−20.5% in vehicle treated Fra2 mice to 40.6+/−15.7% and 25.0+/−20.4% in Fra2 tg mice treated with ADAGEN® (Leadiant Biosciences Ltd., Windsor, UK) in doses of 0.5 and 5 units respectively. The photomicrographs illustrated in FIG. 1, where the data is summarized in graphic form, visually illustrate this point. FIG. 1 photomicrographs demonstrate the effects of ADAGEN® on the occlusion of pulmonary vessels in Fra2 tg mice. Representative images stained with hematoxylin/eosin are shown in 200-fold magnification for each group.

Figure 2:
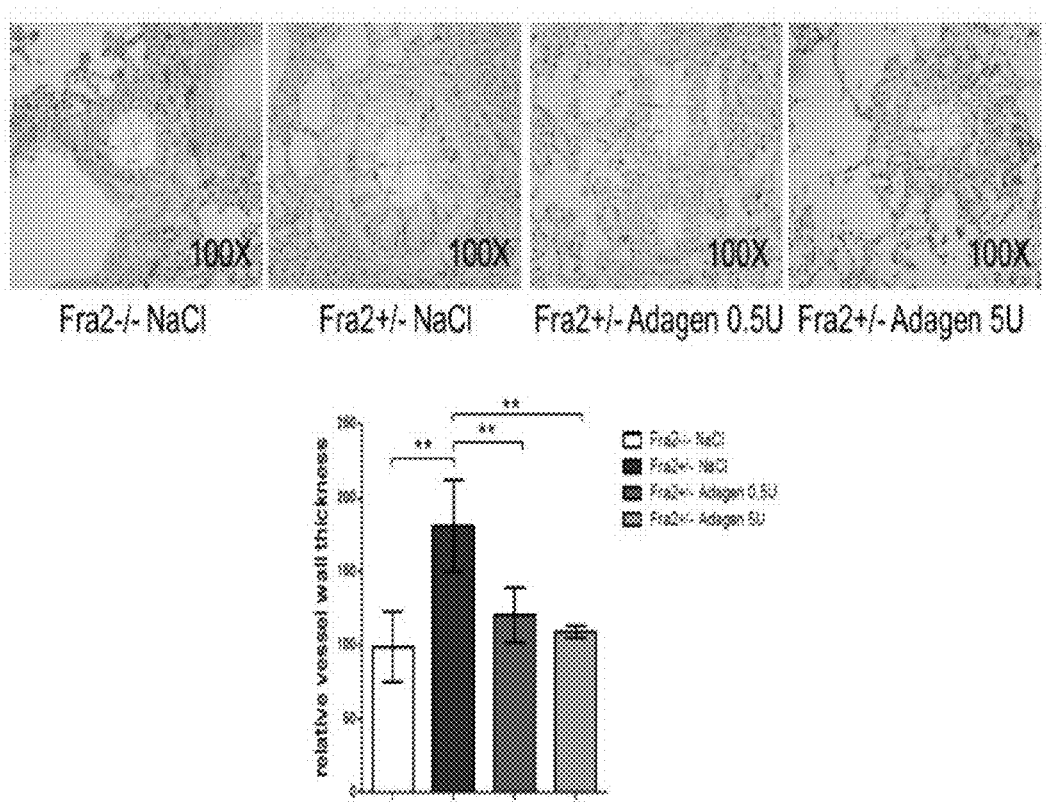
FIG. 2 illustrates images of data, and graphically illustrates data, from experiments showing that the mean vessel wall thickness of the pulmonary arteries in Fra2 tg mice was increased by 1.81+/−0.31 fold compared to non-transgenic control mice ($P<0.01$). Treatment with ADAGEN® pegylated adenosine deaminase (Leadiant Biosciences Ltd., Windsor, UK) significantly decreased thickening of the vessel walls of the pulmonary arteries and reduced the increase in relative vessel wall thickness in Fra2 tg mice to 1.21+/−0.19 at 0.5 U ($P<0.01$ vs NaCl) and to 1.09+/−0.04 fold at ADAGEN® 5 U ($P<0.01$ vs NaCl control).

The photomicrographs illustrated in FIG. 2, where the data is summarized in graphic form, demonstrate the effects of ADAGEN® on vascular lesions in Fra2 tg mice as analyzed by relative vessel wall thickness of the pulmonary arteries. Representative images stained with hematoxylin/eosin are shown in 100-fold magnification for each group.

Another widely used mouse model of systemic sclerosis was also employed in the study, the B10.D2→BALB/c (H-2(d) minor histocompatibility antigen mismatched model, is a model of systemic sclerosis (also known as the sclerodermatous chronic graft versus host disease mouse model or SSc-cGVHD) characterized by similar dermatological and pulmonary pathology. The B10.2D2 (H-2D) mice purchased from Jackson laboratory (Bar Harbor Me.) were maintained in specific pathogen free conditions with sterile pellet food and water on a normal day/night cycle. Unfractionated tibial and femoral derived bone marrow cells were obtained and filtered by usual methods until the time of transplantation Recipient mice (BALB/c (H-2d) 8 weeks old received total body radiation with 700 cGy. Six hours following radiation, all BALB/c (H-2D) recipients received bone marrow from either syngeneic BALB/c (H-2D) mice or from allogeneic B10.D2 (H-2D) mice. Via infusion of 5×10(6) splenocytes and 1×10(6) bone marrow cells resuspended in 0.2 ml of PBS injected via tail veins. Four groups of transplanted mice were begun on treatment starting 10 days post BMT and the mice were sacrificed and samples obtained for analyses 45 days post BMT.

Four groups comprised of eight mice each were studied. The groups were as follows:

Group 1) Syngeneically transplanted control group with application of the solvent of ADA Group 2) Vehicle-treated fibrosis group: Mice who had undergone allogeneic bone marrow and splenocyte transplantation (B10.D2(H-2d→BALB/c(H-2d)

Treatment Group 1) Mice who had undergone allogeneic bone marrow and splenocyte transplantation (B10.D2 (H-2d)→BALB/c (H-2d) treated with ADA low dose (0.5 U 1×/week i.p.)

Treatment Group 2) Allogeneic bone marrow and splenocyte transplantation (B10.D2 (H-2d) treated with high dose ADA (5 U ix/week i.p.)

Outcome Measures:

Clinical score of SSc-cGVHD (an art accepted animal model of systemic sclerosis); Mice with chronic GVHD develop wasting, hunched posture, and alopecia.

A scoring system was used for classification of the degree of SSc-GVHD as follows based on surface area of observed alopecia Healthy appearance=0

Alopecia<1 $cm^2$=1

Alopecia 1-2 $cm^2$=2

Alopecia>2 $cm^2$=3

Additional clinical parameters monitored included mobility, diarrhea, and weight loss. The incidence of clinical cGVHD was expressed as the percentage of mice that showed clinical manifestations.

Figure 3A:
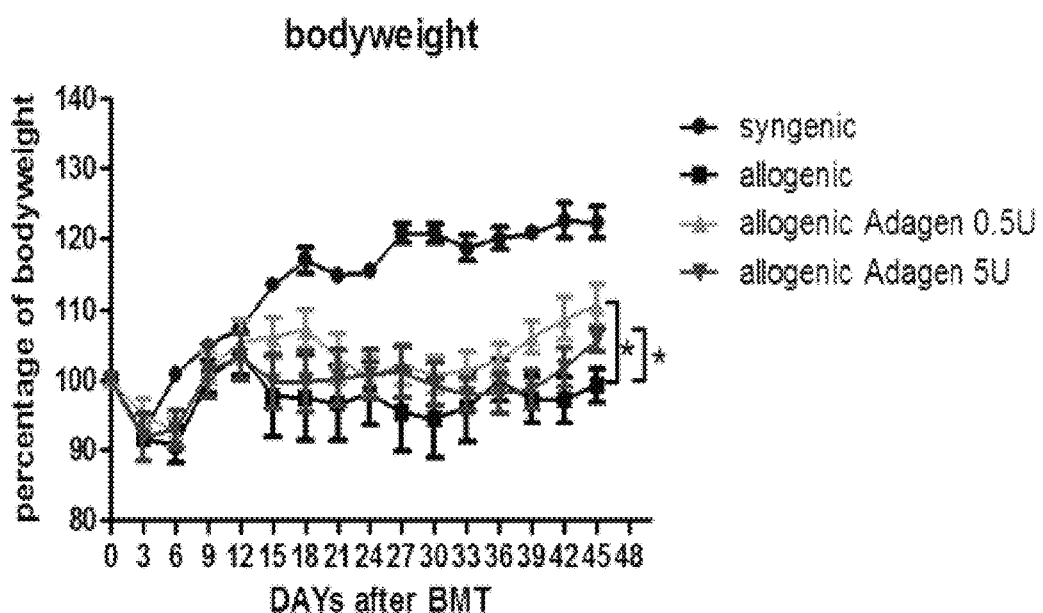
FIG. 3 graphically depicts the effect of ADAGEN® pegylated adenosine deaminase (Leadiant Biosciences Ltd., Windsor, UK) on the clinical outcomes on body weight (FIG. 3A) and clinical composite score (FIG. 3B) in murine sclerodermatous cGvHD.

Allogeneic BMT induced weight loss with a significantly lower mean body weight in allogenically transplanted, vehicle-treated mice compared to syngeneic controls 45 days after BMT (99±5% baseline vs. 122±4% baseline, **). Treatment with ADAGEN at doses of 0.5 U and 5 U partially rescued the weight loss induced by allogeneic BMT and increased the mean body weights to 111±8% and 106±4% baseline, respectively (* for both). See FIG. 3A.

Figure 3B:
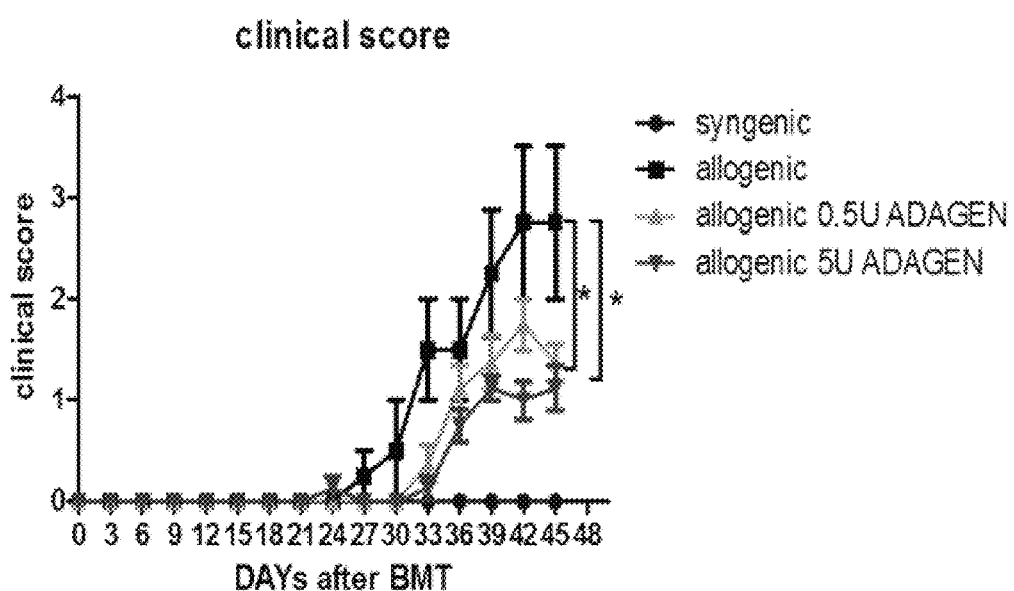

The first clinical signs of disease became evident at 24 days after allogeneic BMT. The composite score of cGvHD progressively increased to 2.75±1.50 in vehicle-treated, allogeneically transplanted mice at 45 days after BMT. In contrast, syngeneically transplanted control mice did not develop any clinical manifestation of disease throughout the observation period (mean score of 0±0). ADAGEN ameliorated clinical signs of cGvHD and reduced the mean composite scores to 1.38±0.52 for mice treated with doses of 0.5 U and to 1.13±0.64 for mice treated with ADAGEN in doses of 5 U (* for both). See FIG. 3B.

ADAGEN® was initially used in animal models of scleroderma to test its pharmacological activity, and the same or substantially the same pharmacological effects are expected to be obtained following the administration of any Adenosine Deaminase (ADA) native protein of human or animal origin, including bovine; and also including: ADA obtained by extraction and purification from tissues; by recombinant or any synthetic or semi-synthetic process; as well as by any peptide or polypeptide with ADA activity, including ADA conjugates.

ADA activity is important to lower the levels of adenosine in blood, plasma, serum, tissues and to trigger a cascade of biochemical events which could result in the amelioration of the clinical manifestations of scleroderma-associated vasculopathies.

ADA, or any peptide or polypeptide with ADA activity, including ADA conjugates, which can lower levels of adenosine in blood, plasma, serum, tissues, are effective in the prevention or decrease of progression of scleroderma and associated vascular conditions; and is effective in arresting, treating, ameliorating or preventing scleroderma-associated vasculopathies and vascular changes, in particular a proliferative obliterative vasculopathy such as idiopathic obliterative vasculopathy and progressive obliterative vasculopathy, Raynaud's syndrome, edematous puffy hands, telangiectasias, digital ulcers, pulmonary arterial hypertension (PAH), myocardial dysfunction, and scleroderma renal crisis.

In summary, these data demonstrate the value of ADA (including ADA conjugates) in affecting (decreasing) the vascular wall thickness (or preventing the occurrence of, or decreasing the severity of, scleroderma-related vascular wall thickening) of sclerodermatous arteries, as well as decreasing or preventing the vascular thromboses that are an important feature of this serious and often fatal disease.

In summary, these data demonstrate the value of ADA treatment (including ADA conjugates) in improving the underlying vasculopathy that is a significant component of the disease in a well-accepted model of scleroderma (Fra2 mouse). ADA dramatically affected the proliferative vasculopathy and vascular intimal thickening which are not only responsible for many of the morbidities seen in scleroderma and are thought by many experts to be a critical component of the pathophysiology of the disease. Preventive treatment with ADA also slowed the progression of disease in the SSc-cGVHD model and improved clinical features when given at very early stages of the disease.

Adenosine Deaminase (ADA) Enzymes

In alternative embodiments, provided are compositions and methods using Adenosine Deaminase (ADA) enzymes, or polypeptides or peptides having ADA activity, including ADA conjugates, which can be from human or non-human, e.g., animal such as bovine, sources or recombinant or synthetic ADA. In alternative embodiments, enzymes used include ADA polypeptides or active fragments thereof, including analogs, mutations, derivatives or chemical modifications thereof, including for example, conjugates, capped forms or multiple or mono-pegylations as described below, or as described in U.S. Pat. No. 8,071,741. For example, in one embodiment, if the ADA is purified from a bovine source, the Cys 74 residue of the naturally occurring bovine ADA is capped or protected by a cysteine and the six C-terminal residues predicted from the gene encoding the ADA of SEQ ID NO:1 are not present.

In alternative embodiments, ADA or polypeptides or peptides having ADA activity, are recombinant forms. In alternative embodiments, ADA can be a recombinant bovine ADA (SEQ ID NO: 1) or a recombinant human ADA ("rhADA", SEQ ID NO:3) translated from a DNA molecule according to SEQ ID NO:2 or SEQ ID NO:4. In alternative embodiments, the recombinant ADA can lack the six C-terminal residues of the bovine ADA, e.g., as described in U.S. Pat. No. 8,071,741.

In alternative embodiments, ADA or polypeptides or peptides or agonists having ADA activity, are mutations, analogs, derivative, chemical modifications, variants or conjugates as described e.g., U.S. Patent Application Publication no. 20080159964 A1 and U.S. Pat. No. 8,071,741. For example, alternative embodiments, ADA can be stabilized by capping a solvent-exposed oxidizable Cys residue; an oxidizable amino acid such as cysteine residue of the recombinant ADA can be capped by the capping agent such as oxidized glutathione, iodoacetamide, iodoacetic acid, cystine, other dithiols and mixtures thereof without substantially inactivating the ADA protein. The capping of the recombinant ADA stabilizes and protects the ADA from degradation. In alternative embodiments, in ADA or polypeptides or peptides having ADA activity, an oxidizable Cys residue that is solvent-exposed is replaced with a suitable non-oxidizable amino acid residue, e.g., alanine, serine, asparagine, glutamine, glycine, isoleucine, leucine, phenylalanine, threonine, tyrosine, and valine.

Adenosine Deaminase (ADA) Conjugates

In alternative embodiments, provided are Adenosine Deaminase (ADA) enzymes, or polypeptides or peptides having ADA activity, conjugated to another molecule, e.g., a polyethylene glycol or other polymer, including any non-antigenic (e.g., non-antigenic to a human) polymer, gelatin, or nanoparticles.

In alternative embodiments, ADA-polyethylene glycol conjugates used to practice methods as provided herein are prepared using the techniques described in U.S. Pat. Nos. 4,179,337; 5,122,614; 5,324,844; U.S. Pat. No. 5,349,001; and, U.S. Pat. No. 5,728,650, which describe how to form a substantially hydrolysis-resistant urethane bond between the epsilon amino groups of enzymes and a functionalized terminal group. The linkage by which the ADA enzyme or polypeptide or peptide having ADA activity is joined to the polymer strand(s) can be any moiety known in the art which sufficiently unites the enzyme or polypeptide and polymer so that the conjugate may be administered in a pharmaceutically acceptable manner. In alternative embodiments, amide linkages are used. An example of amide-linked polymer enzymes that can be used is found in U.S. Pat. No. 5,349,001, which describes use of cyclic imide-activated polyalkylene oxides and conjugation thereof with therapeutic proteins and enzymes including ADA.

In alternative embodiments, non-antigenic polymeric substances include materials such as dextran, polyvinyl pyrrolidones, polysaccharides, starches, polyvinyl alcohols, polyacryl amides or other similar non-immunogenic polymers.

In alternative embodiments, to prepare an ADA, or a polypeptide or peptide having ADA activity, for conjugation, epsilon amino group modifications of lysines, or modifications of carboxylic acid groups, and/or other reactive amino acid groups are prepared as well-known in the art.

In alternative embodiments, conjugates are from between about 1 to about 25 polymeric strands attached to each molecule of the ADA, or a polypeptide or peptide having ADA activity. By controlling the molar excess of the polymer reacted with the enzyme, the number of polymeric strands attached can be varied. For example, in alternative embodiments, conjugates comprise from between about 5 to about 20 polymeric strands, or from about 10 to 18 polymeric strands as well-known in the art.

In alternative embodiments, ADA, or a polypeptide or peptide having ADA activity, is conjugated to a polyalkylene oxide, such as polyethylene glycol, which can be straight, branched or multi-arm polymers; optionally polyalkylene oxides and polyethylene glycols (PEGs) have molecular weights (MWs) ranging from between about 2,000 to about 45,000 daltons, see for example U.S. Pat. No. 8,071,841; e.g., the ADA when conjugated to a polyethylene glycol is ADAGEN® (Leadiant Biosciences, Windsor, UK).

In alternative embodiments, the polypeptide having ADA activity is a poly(oxy-1,2-ethanediyl), α-carboxy-ω-methoxy-, amide with adenosine deaminase, e.g., a synthetic ADA (one form of which has been given the name elapegademase or EZN2279), where the ADA can have the sequence (SEQ ID NO: 1):

AQTPAFNKPKVELHVHLDGAIKPETILYYGRKRGIALPADTPEELQNIIG

MDKPLSLPEFLAKFDYYMPAIAGSREAVKRIAYEFVEMKAKDGVVYVEVR

YSPHLLANSKVEPIPWNQAEGDLTPDEVVSLVNQGLQEGERDFGVKVRSI

LCCMRHQPSWSSEVVELCKKYREQTVVAIDLAGDETIEGSSLFPGHVKAY

AEAVKSGVHRTVHAGEVGSANVVKEAVDTLKTERLGHGYHTLEDTTLYNR

LRQENMHFEVCPWSSYLTGAWKPDTEHPVVRFKNDQVNYSLNTDDPLIFK

STLDTDYQMTKNEMGFTEEEFKRLNINAAKSSFLPEDEKKELLDLLYKAY

GMPSPA.

The above mentioned ADA is codified by a DNA, where the DNA can have the sequence (SEQ ID No. 2):

```
atggctcaga ccccggcttt caacaaaccg aaggtagaac
tgcacgtaca cctggatggt gctatcaaac cggagactat
cctgtactat ggtcgtaagc gtggcatcgc tctgccggct
gacactccgg aagaactgca gaacatcatc ggcatggaca
aaccgctgtc tctgccggaa ttcctggcta aattcgacta
ctacatgccg gctatcgctg gttctcgtga agcagtcaaa
cgtatcgctt acgaattcgt agaaatgaaa gctaaagatg
gtgtagtata cgttgaagtt cgttactctc cgcacctgct
ggcaaactct aaagttgaac cgatcccgtg gaaccaggca
gaaggcgatc tgactccgga tgaagtagtt ctctggtta
accagggtct gcaggaggt gaacgcgatt cggcgtaaa
agttcgttct atcctgtgct gcatgcgcca ccagccgtct
tggtcttctg aagttgttga actgtgcaag aaataccgtg
agcagaccgt agttgctatc gatctggcag gtgatgaaac
catcgaaggt tcttctctgt ttccgggtca cgtaaaggct
tatgctgaag ctgttaaatc tggcgtacac cgtactgtac
acgcaggtga agttggtct gctaacgttg ttaaagaagc
tgttgacacc ctgaaaactg aacgcctggg tcacggctac
cacaccctgg aagacaccac cctgtacaac cgtctgcgtc
aggaaaacat gcacttcgaa gtttgtccgt ggtcctctta
cctgactggt gcttggaaac cggacaccga acaccggtt
gttcgtttca aaacgacca ggtaaactac tctctgaaca
ctgacgatcc gctgatcttc aaatctaccc tggacaccga
ctaccagatg accaaaaacg aaatgggttt cactgaagaa
```
gaattcaaac gtctgaacat caacgctgct aagtcctctt ttctgccgga agatgagaaa aaagaactgc tggacctgct gtacaaggca tacggtatgc cgtctccggc ttaa.

In alternative embodiments, the polypeptide having ADA activity is a recombinant human protein, which can have the sequence (SEQ ID NO. 3):

AQTPAFDKPKVELHVHLDGSIKPETILYYGRRRGIALPANTAEGLLNVIG

MDKPLTLPDFLAKFDYYMPAIAGSREAIKRIAYEFVEMKAKEGVVYVEVR

YSPHLLANSKVEPIPWNQAEGDLTPDEVVALVGQGLQEGERDFGVKARSI

LCCMRHQPNWSPKVVELCKKYQQQTVVAIDLAGDETIPGSSLLPGHVQAY

QEAVKSGIHRTVHAGEVGSAEVVKEAVDILKTERLGHGYHTLEDQALYNR

LRQENMHFEICPWSSYLTGAWKPDTEHAVIRLKNDQANYSLNTDDPLIFK

STLDTDYQMTKRDMGFTEEEFKRLNINAAKSSFLPEDEKRELLDLLYKAY

GMPPSASAGQNL

The above mentioned ADA of SEQ ID NO. 3 is codified by a DNA, where the DNA can have the sequence (SEQ ID No. 4):

```
atggctcaga cacccgcatt tgataaaccg aaagtggaac
tgcatgtcca cctggatggt agcatcaaac cggaaactat
cttatattac ggtcggcgtc gtggtattgc gttgccggca
aacacggctg aaggtttgct gaacgtgatc ggcatggaca
aaccgctgac cttgccggat ttttggcga aatttgatta
ttatatgccg gcgattgctg gttcccgcga ggcaatcaaa
cgcatcgcgt atgagtttgt tgaaatgaaa gcgaaagaag
gcgttgtgta tgttgaggtc cgttacagtc cgcatctgct
ggctaacagc aaggtagaac ctatcccctg gaaccaagct
gaaggcgatc tgacgccgga tgaagtggtt gctctggtgg
gtcagggttt acaggagggg gagcgcgatt ttggcgttaa
agctcgctct attttatgtt gcatgcgcca tcagcccaat
tggtccccga aagtggttga actttgtaaa aagtaccaac
aacagaccgt tgtcgcgatt gatttggcag gcgatgaaac
aattccaggc agctccctgt tgccagggca cgtgcaagcg
taccaagaag cagtgaaaag cggcatccac cggactgtcc
acgccggcga ggtcggtagc gccgaggttg tgaaagaagc
cgtggacatc ctgaaaaccg agcggctggg ccatgggtac
cacacactgg aggatcaggc attatataac cgcttacgcc
aggaaaatat gcatttcgaa atttgtccgt ggagtagtta
cttaactggc gcgtggaaac cggataccga acatgcggtt
atccgcttaa agaatgatca agcaaattac agtctgaata
cagatgatcc cctgattttc aagtctaccc tggacacaga
```

```
ttatcagatg acgaagcggg atatgggatt tacggaagaa gaatttaagc gtctcaatat caatgcggcg aaatcttcat ttctgccgga agatgagaaa cgtgagttgc tggatcttct gtacaaggcc tacggtatgc cgccgagcgc atcggccggg cagaacctg
```

In alternative embodiments, the polypeptide having ADA activity is conjugated with either of:
or

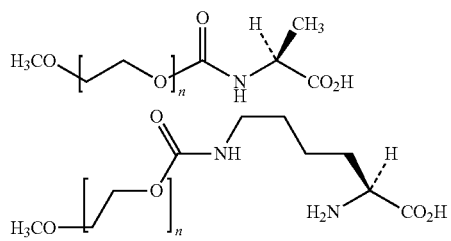

wherein n is a positive integer between 1 and 5,000, preferably between 1 and 4,000, more preferably between 1 and 2,500, in particular between 18 and 2,269.

In alternative embodiments, the polypeptide having ADA activity is described in U.S. Pat. No. 8,071,741.

In alternative embodiments, ADA or polypeptides or peptides having ADA activity, are conjugates having the general formula:

[R—NH]$_z$-(ADA)

where z is a positive integer, e.g., from about 1 to about 80; and R comprises a polymer, e.g., a substantially non-antigenic polymer, which can be in a releasable or non-releasable form. In alternative embodiments, the polymer is a polyethylene glycol (PEG), where the PEG can be a linear, branched or a multi-armed PEG. In alternative embodiments, average MW of the polymers ranges from an average 1000 to 100,000 Da, or from about 5,000 Da to about 45,000 Da, or 5,000 Da to about 20,000 Da, or about 5,000 Daltons, as is found in ADAGEN®.

In alternative embodiments, the PEG can be functionalized as:

—C(=Y$_{74}$)—(CH$_2$)$_m$—(CH$_2$CH$_2$O)$_n$—,

—C(=Y$_{74}$)—Y—(CH$_2$)$_m$—(CH$_2$CH$_2$O)$_n$—,

—C(=Y$_{74}$)—NR$_{11}$—(CH$_2$)$_m$—(CH$_2$CH$_2$O)$_n$—,

—CR$_{75}$R$_{76}$—(CH$_2$)$_m$—(CH$_2$CH$_2$O)$_n$— where R$_{11}$, R$_{75}$ and R$_{76}$ are independently selected from among H, C$_{1-6}$ alkyls, aryls, substituted aryls, aralkyls, heteroalkyls, substituted heteroalkyls and substituted C$_{1-6}$ alkyls; m is zero or is a positive integer, e.g., 1 or 2; Y$_{74}$ is O or S; and n represents the degree of polymerization.

In alternative embodiments, releasable polymer systems can be based on benzyl elimination or trimethyl lock lactonization. Activated polymer linkers of releasable polymer systems can be prepared e.g., as described in U.S. Pat. Nos. 6,180,095; 6,720,306; 5,965,119; 6,624,142; and 6,303,569. In alternative embodiments, an ADA polymer conjugate is made using certain bicine (2-(Bis(2-hydroxyethyl) amino) acetic acid) polymer residues such as those described in U.S. Pat. Nos. 7,122,189 and 7,087,229. In alternative embodiments, activated PEGs as described in U.S. Pat. Nos. 5,122,614; 5,324,844; 5,612,460; and 5,808,096, are used. In alternative embodiments, a polyalkylene oxide is conjugated to an ADA via linker chemistry including, e.g., succinimidyl carbonate, thiazolidine thione, urethane, and amide based linkers. In alternative embodiments, polyalkylene oxide is covalently attached to an epsilon amino group of a Lys on the ADA purified from bovine or the cysteine-stabilized recombinant human ADA. In alternative embodiments, capped ADA polymer conjugates comprise at least 5 polyethylene glycol strands attached to epsilon amino groups of Lys on the enzyme, have between about 11 to 18 PEG strands attached to epsilon amino groups of Lys on the enzyme.

Pharmaceutical Compositions and Formulations

In alternative embodiments, provided are pharmaceutical compositions and formulations for practicing the uses and methods as provided herein, e.g., methods for treating, ameliorating, reversing, slowing the progression of, or abating or diminishing the symptoms of, or preventing: scleroderma-associated vasculopathies and vascular changes, in particular a proliferative obliterative vasculopathy such as idiopathic obliterative vasculopathy and progressive obliterative vasculopathy, Raynaud's syndrome, edematous puffy hands, telangiectasias, digital ulcers, pulmonary arterial hypertension (PAH), myocardial dysfunction, and scleroderma renal crisis; in an individual in need thereof; or, arresting, treating, ameliorating, slowing the progression of or preventing Raynaud's syndrome, nonpitting edema of the hands, distal finger ulcers and/or facial or peri-oral skin tightening with decreased oral aperture, wherein the Raynaud's syndrome, nonpitting edema of the hands, distal finger ulcers and/or facial or peri-oral skin tightening are early pathological expressions of scleroderma.

In alternative embodiments, pharmaceutical compositions and formulations comprise an Adenosine Deaminase (ADA), or a polypeptide or peptide having Adenosine Deaminase activity, for example, an ADA manufactured as or is formulated in an ADA conjugate form, e.g., as a polyethylene glycol conjugate form, e.g., as a PEGylated bovine adenosine deaminase enzyme, or a (monomethoxypolyethylene glycol succinimidyl) 11-17-adenosine deaminase, or ADAGEN® (Leadiant Biosciences Ltd., Windsor, UK).

In alternative embodiments, compositions used to practice the uses and methods as provided herein, are formulated with a pharmaceutically acceptable carrier. In alternative embodiments, the pharmaceutical compositions used to practice the uses and methods as provided herein can be administered parenterally, topically, subcutaneously, intramuscularly, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, e.g., the latest edition of Remington's Pharmaceutical Sciences, Mack Publishing Co, Easton Pa. ("Remington's").

Therapeutic agents used to practice the uses and methods as provided herein can be administered alone or as a component of a pharmaceutical formulation (composition). The compounds may be formulated for administration in any convenient way for use in human or veterinary medicine.

Wetting agents, emulsifiers and lubricants, such as sodium lauryl sulfate and magnesium stearate, as well as coloring agents, release agents, coating agents, sweetening, flavoring and perfuming agents, buffers, preservatives and antioxidants can also be present in the compositions.

Formulations of the compositions used to practice the uses and methods as provided herein include those suitable for oral/nasal, topical, parenteral, preferably intramuscular, injection; rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

Pharmaceutical formulations used to practice the uses and methods as provided herein can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, geltabs, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations used to practice the uses and methods as provided herein can also be used orally using, e.g., push-fit capsules made of gelatin, as well as soft, sealed capsules made of gelatin and a coating such as glycerol or sorbitol. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., a composition used to practice the uses and methods as provided herein) in admixture with excipients suitable for the manufacture of aqueous suspensions. Such excipients include a suspending agent, such as sodium carboxymethylcellulose, methylcellulose, hydroxypropyl-methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin, or erythritol or rebaudioside A. Formulations can be adjusted for osmolarity.

Oil-based pharmaceuticals are particularly useful for administration hydrophobic active agents used to practice the uses and methods as provided herein. Oil-based suspensions can be formulated by suspending an active agent in a vegetable oil, such as *arachis* oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858, 401). The oil suspensions can contain a thickening agent, such as beeswax, hard paraffin or cetyl alcohol. Sweetening agents can be added to provide a palatable oral preparation, such as glycerol, sorbitol or sucrose, or erythritol or rebaudioside A. These formulations can be preserved by the addition of an antioxidant such as ascorbic acid. As an example of an injectable oil vehicle, see Minto (1997) J. Pharmacol. Exp. Ther. 281:93-102. The pharmaceutical formulations as provided herein can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

In practicing uses and methods provided herein, the pharmaceutical compounds can also be administered by in intranasal, intraocular and intravaginal routes including suppositories, insufflation, powders and aerosol formulations (for examples of steroid inhalants, see Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In practicing uses and methods provided herein, the pharmaceutical compounds can be delivered by transdermally, by a topical route, formulated as applicator sticks, solutions, suspensions, emulsions, gels, creams, ointments, pastes, jellies, paints, powders, and aerosols.

In practicing methods provided herein, the pharmaceutical compounds can be delivered by inhalation; for example, in alternative embodiments ADA or ADA conjugates, e.g., PEG-conjugates for inhalation are prepared for dry dispersal, for example, by spray drying a solution containing ADA or ADA PEG-conjugate, e.g., using methods as described in U.S. Pat. Nos. 6,509,006; 6,592,904; 7,097,827; and 6,358,530. Exemplary dry powder excipients include a low molecular weight carbohydrates or polypeptides to be mixed with the ADA or ADA PEG-conjugate to aid in dispersal. In alternative embodiments, types of pharmaceutical excipients that are useful as carriers for dry powder dispersal include stabilizers such as human serum albumin (HSA), that is also a useful dispersing agent, bulking agents such as carbohydrates, amino acids and polypeptides; pH adjusters or buffers; salts such as sodium chloride; and the like. These carriers may be in a crystalline or amorphous form or may be a mixture of the two. Devices that can be used to deliver powder or aerosol formulations include those as described e.g., in U.S. Pat. Nos. 5,605,674; 7,097,827, for example, the devices can be nebulizers.

In practicing methods provided herein, the pharmaceutical compounds can also be delivered as nanoparticles or microspheres for slow release in the body. For example, nanoparticles or microspheres can be administered via intradermal or subcutaneous injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In practicing methods provided herein, the pharmaceutical compounds can be parenterally administered, such as by intramuscular (IM), intrathecal, or intravenous (IV) administration or administration into a body cavity or lumen of an organ. These formulations can comprise a solution of active agent dissolved in a pharmaceutically acceptable carrier. Acceptable vehicles and solvents that can be employed are water, dextrose in water, and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

The pharmaceutical compounds and formulations used to practice the uses and methods as provided herein can be lyophilized. Provided are a stable lyophilized formulation comprising a composition as provided herein, which can be made by lyophilizing a solution comprising a pharmaceutical as provided herein and a bulking agent, e.g., mannitol, trehalose, raffinose, and sucrose or mixtures thereof. There are many other conventional lyophilizing agents. Among the sugars, lactose is the most common. Also used are citric acid, sodium carbonate, EDTA, Benzyl alcohol, glycine, sodium chloride, etc. (see for example Journal of Excipients and Food Chemistry Vol. 1, Issue 1 (2010) pp 41-54). A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. patent app. no. 20040028670.

The formulations used to practice the uses and methods as provided herein can be administered for prophylactic and/or therapeutic treatments. In therapeutic applications, compositions are administered to a subject already suffering from a condition, or disease in an amount sufficient to cure, alleviate or partially arrest the clinical manifestations of the condition, or disease and its complications (a "therapeutically effective amount"). For example, in alternative embodiments, pharmaceutical compositions as provided herein are administered in an amount sufficient to for e.g., the prevention and treatment of scleroderma-associated vasculopathies and vascular changes, in particular a proliferative obliterative vasculopathy such as idiopathic obliterative vasculopathy and progressive obliterative vasculopathy, causing structural and functional abnormalities such as Raynaud's syndrome, edematous puffy hands, telangiectasias, digital ulcers, pulmonary arterial hypertension (PAH), myocardial dysfunction, and scleroderma renal crisis in an individual in need thereof. The amount of pharmaceutical composition adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. The dosage schedule can be adjusted also by monitoring the relevant biomarkers. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods as provided herein are correct and appropriate.

Single or multiple administrations of formulations can be given depending on the dosage and frequency as required and tolerated by the patient. The formulations should provide a sufficient quantity of active agent to effectively treat, prevent or ameliorate a conditions, diseases or symptoms as described herein. For example, an exemplary pharmaceutical formulation for oral administration of compositions used to practice the methods as provided herein can be in a daily amount of between about 0.1 to 0.5 to about 20, 50, 100 or 1000 or more µg per kilogram of body weight per day.

In an alternative embodiment, dosages are from about 1 mg to about 4 mg per kg of body weight per patient per day are used. In alternative embodiments, an effective amount of Adenosine Deaminase (ADA), or the polypeptide or peptide having ADA activity, administered to an individual in need thereof is: from about 0.01 to about 100 mg/kg, or about 1 to about 100 mg/kg, or from about 5 to about 50 mg/kg, or from about 10 to about 30 mg/kg; from about 5 U/kg to about 50 U/kg, or from about 10 U/kg to about 30 U/kg; or from about 0.5 U/kg to about 5 U/kg (e.g., about 1 U/kg), or, about 250 units/ml administered at various intervals (daily, weekly, biweekly, triweekly, monthly), optionally administered IV, IM or subcutaneously. Suraphysiological doses can also be provided, for example up to about 100 U/kg or more.

In alternative embodiments, an effective amount of Adenosine Deaminase (ADA), or the polypeptide or peptide having ADA activity, administered to an individual in need thereof comprises use of various dosaging schedules, e.g.:
  dosing schedule is about 10 U/kg, or between about 5 to 15 U/kg, ADAGEN® (or about 0.067 mg/kg, or between about 0.001 to 0.12 mg/kg or between about 0.03 to 0.12 mg/kg, EZN2279) for the first dose;
  about 15 U/kg, or between about 5 to 15 U/kg, ADAGEN® (or about 0.1 mg/kg or between about 0.05 to 0.5 mg/kg, EZN2279) for the second dose,
  about 30 U/kg ADAGEN®, or about 20 U/kg ADAGEN®, or between about 15 to 30 U/kg, between about 15 to 25 U/kg (or about 0.134 mg/kg, or between about 0.05 to 0.30 mg/kg, or between about 0.05 to 0.25 mg/kg EZN2279) for the third dose. Suraphysiological doses can also be provided, for example up to 100 U/kg, or more.

In alternative embodiments, a maintenance dose is administered, e.g., about 20 U/kg per week, or between about 15 to 25 U/kg per week, for ADAGEN® (or about 0.134, or between about 0.05 to 0.25 mg/kg, mg/kg EZN2279), with further increases of about 5, or between about 1 and 10, U/kg/week if necessary, but for some patients a maximum single dose of about 30 U/kg ADAGEN® (or about 0.2 mg/kg EZN2279) should not be exceeded. However, if needed or wished, suraphysiological doses may also be provided, for example up to 100 U/kg, or higher, as the "dosing regimen," will depend upon a variety of factors, including the stage of the disease or condition, the severity of the disease or condition, the general state of the patient's health, the patient's physical status, age and the like.

In alternative embodiments, an effective amount of Adenosine Deaminase (ADA), or the polypeptide or peptide having ADA activity, administered to an individual in need thereof is individualized based on monitoring of plasma ADA activity after initial administrations.

In alternative embodiments, an effective amount of Adenosine Deaminase (ADA), or the polypeptide or peptide having ADA activity, administered to an individual in need thereof is an amount sufficient to maintain plasma ADA activity (trough levels) in the range of from between about 250 U/L to about 580 U/L (assayed at 37° C.), or in the range of from between about 10 U/L to about 50 U/L or in the range of between about 10 U/L to about 600 U/L.

In alternative embodiments, an effective amount is demonstrated by a decline in adenosine in the form of plasma adenosine. In alternative embodiments, an effective amount of Adenosine Deaminase (ADA), or the polypeptide or peptide having ADA activity, or ADA conjugates, administered to an individual in need thereof is an amount sufficient to reduce vascular tissue adenosine levels (where adenosine is present in the form of AMP, ADP, ATP) to less than about 10 nmoles per mg protein, or to less than about 5 nmoles per mg protein.

In alternative embodiments, lower dosages of ADA, or the polypeptide or peptide having ADA activity, including ADA conjugates, are used when administered in the blood stream or IV or IM (in contrast to administration e.g., orally, by inhalation or subcutaneously) e.g., as an IV or an IM administration, or into a body cavity or into a lumen of an organ. Substantially higher dosages can be used in topical, spray, inhalation or oral administration or administering by powders, spray or inhalation. Actual methods for preparing parenterally or non-parenterally administrable formulations will be known or apparent to those skilled in the art and are described in more detail in such publications as Remington's, supra.

In alternative embodiments, ADA, or the polypeptide or peptide having ADA activity, including ADA conjugates, are given chronically, e.g., from day of diagnosis and until the last day of a patient's life or until the disease has abated. In alternative embodiments, dose adjustments are required moving from a treatment phase to a maintenance period through the periodic monitoring of specific, conventionally known biomarkers of the disease.

In alternative embodiments, in evaluating the efficacy of a treatment, a treatment regimen or a particular dosage, or to determine if a treatment versus a maintenance dosage should be given, individuals, e.g., scleroderma patients, are subject to regular periodic screening for presence and extent of organ and tissue involvement, e.g., including the Rodnan skin score for cutaneous complication, radiography and/or high resolution CT scanning to monitor interstitial fibrosis, echocardiography with Doppler examination to monitor pulmonary hypertension and, blood and urine tests to monitor renal parameters and, if cardiac disease is suspected, serum troponin, creatine kinase MB fraction, and N-terminal pro-brain natruietic peptide, lung function, e.g. FVC. A thorough physical examination should be done at a time interval chosen by those experts in the treatment of systemic sclerosis which would concentrate on cutaneous findings such as digital ulcers, non-pitting edema, telangiectasias, calcinosis cutis and presence and severity of Raynaud's syndrome. Blood pressure is carefully monitored due to the high incidence of renal involvement and the history and physical examination would also concentrate on pulmonary, rheumatic, and gastrointestinal signs and symptoms.

If, in the course of careful clinical and laboratory observation, progression of cutaneous or visceral symptoms of scleroderma are found, one might consider restarting the ADA, or the polypeptide or peptide having ADA activity, or ADA conjugate, at full dose for at least one year before attempting a taper. In some patients, it is likely that the administration of ADA, or the polypeptide or peptide having ADA activity, will need to be chronic and would be justified by the high morbidity and mortality associated with systemic sclerosis.

If residual symptoms remain once the patient is on ADA therapy, a physician skilled in the treatment of scleroderma could use concomitant organ based therapy. For example, in alternative embodiments ADA is administered with topical nitrates or calcium channel blockers for Raynaud's syndrome, antihistamines for pruritus, H2 blockers or proton pump inhibitors for esophageal symptoms, anti-diarrheal agents or anti-spasmotics for lower GI symptoms and ACE-IARB medications for hypertension or other renal manifestations of systemic sclerosis. If, despite ADA and symptomatic treatment there has not been an adequate response, in alternative embodiments immunosuppressive agents combining such agents as methotrexate, cyclophosphamide, mycophenolate mofetil, or rituximab are also used (with a use and method as provided herein) for a rapidly progressing skin disease or pulmonary fibrosis, since they have been shown to have some effectiveness in various clinical studies.

The uses and methods as provided herein can further comprise co-administration with other drugs or pharmaceuticals, e.g., compositions for treating an autoimmune disease or condition, a cancer, septic shock, an infection, fever, pain and related symptoms or conditions. For example, the methods and/or compositions and formulations as provided herein can be co-formulated with and/or co-administered with antibiotics (e.g., antibacterial or bacteriostatic peptides or proteins), particularly those effective against gram negative bacteria or other species causing intestinal bacterial overgrowth, fluids, cytokines, immunoregulatory agents, anti-inflammatory agents, complement activating agents, such as peptides or proteins comprising collagen-like domains or fibrinogen-like domains (e.g., a ficolin), carbohydrate-binding domains, and the like and combinations thereof.

Nanoparticles, Nanolipoparticles and Liposomes

Also provided are nanoparticles, nanolipoparticles, vesicles and liposomal membranes comprising compounds used to practice the uses and methods as provided herein, e.g., to deliver compositions as provided herein (which can comprise an Adenosine Deaminase (ADA), or a polypeptide or peptide having ADA activity or ADA conjugate) to mammalian cells in vivo, in vitro or ex vivo. In alternative embodiments, these compositions are designed to target specific molecules, including biologic molecules, such as polypeptides, including cell surface polypeptides, e.g., for targeting a desired cell type, e.g., a vascular cell (e.g., a vascular endothelial, epithelial or smooth muscle cell), a fibroblast, a myocyte or heart cell, an endothelial cell, and the like.

Provided are multilayered liposomes comprising compounds used to practice methods as provided herein, e.g., as described in Park, et al., U.S. Pat. Pub. No. 20070082042. The multilayered liposomes can be prepared using a mixture of oil-phase components comprising squalane, sterols, ceramides, neutral lipids or oils, fatty acids and lecithins, to about 200 to 5000 nm in particle size, to entrap a composition used to practice uses and methods as provided herein.

Liposomes can be made using any method, e.g., as described in U.S. Pat. No. 4,534,899; or Park, et al., U.S. Pat. Pub. No. 20070042031, including method of producing a liposome by encapsulating an active agent (e.g., an Adenosine Deaminase (ADA), or a polypeptide or peptide having ADA activity or ADA conjugate), the method comprising providing an aqueous solution in a first reservoir; providing an organic lipid solution in a second reservoir, and then mixing the aqueous solution with the organic lipid solution in a first mixing region to produce a liposome solution, where the organic lipid solution mixes with the aqueous solution to substantially instantaneously produce a liposome encapsulating the active agent; and immediately then mixing the liposome solution with a buffer solution to produce a diluted liposome solution.

In one embodiment, liposome compositions used to practice uses and methods as provided herein comprise a substituted ammonium and/or polyanions, e.g., for targeting delivery of a compound (e.g., an Adenosine Deaminase (ADA), or a polypeptide or peptide having ADA activity or ADA conjugate) used to practice methods as provided herein to a desired cell type (e.g., an endothelial cell, a cancer cell, or any tissue in need thereof), as described e.g., in U.S. Pat. Pub. No. 20070110798.

Provided are nanoparticles comprising compounds (e.g., an Adenosine Deaminase (ADA), or a polypeptide or peptide having ADA activity or ADA conjugate) used to practice uses and methods as provided herein in the form of active agent-containing nanoparticles (e.g., a secondary nanoparticle), as described, e.g., in U.S. Pat. Pub. No. 20070077286. In one embodiment, provided are nanoparticles comprising a fat-soluble active agent used to practice a use and method as provided herein or a fat-solubilized water-soluble active agent to act with a bivalent or trivalent metal salt.

In one embodiment, solid lipid suspensions can be used to formulate and to deliver compositions used to practice uses and methods as provided herein to mammalian cells in vivo, in vitro or ex vivo, as described, e.g., in U.S. Pat. Pub. No. 20050136121.

The compositions and formulations used to practice the uses and methods as provided herein can be delivered by the use of liposomes or nanoliposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587.

Delivery Vehicles

In alternative embodiments, any delivery vehicle can be used to practice the uses and methods as provided herein, e.g., to deliver compositions methods as provided herein (e.g., an Adenosine Deaminase (ADA), or a polypeptide or peptide having ADA activity or ADA conjugate) to mammalian cells in vivo, in vitro or ex vivo. For example, delivery vehicles comprising polycations, cationic polymers and/or cationic peptides, such as polyethyleneimine derivatives, can be used e.g. as described, e.g., in U.S. Pat. Pub. No. 20060083737.

In one embodiment, a dried polypeptide-surfactant complex is used to formulate a composition used to practice a use and method as provided herein, e.g. as described, e.g., in U.S. Pat. Pub. No. 20040151766.

In one embodiment, a composition used to practice uses and methods as provided herein can be applied to cells using vehicles with cell membrane-permeant peptide conjugates, e.g., as described in U.S. Pat. Nos. 7,306,783; 6,589,503. In one aspect, the composition to be delivered is conjugated to a cell membrane-permeant peptide. In one embodiment, the composition to be delivered and/or the delivery vehicle are conjugated to a transport-mediating peptide, e.g., as described in U.S. Pat. No. 5,846,743, describing transport-mediating peptides that are highly basic and bind to polyphoshoinositides.

In one embodiment, electro-permeabilization is used as a primary or adjunctive means to deliver the composition to a cell, e.g., using any electroporation system as described e.g. in U.S. Pat. Nos. 7,109,034; 6,261,815; 5,874,268.

Products of Manufacture and Kits

In alternative embodiments, provided are products of manufacture and kits comprising an Adenosine Deaminase (ADA), or a polypeptide or peptide having ADA activity, or ADA conjugate, for practicing uses and methods as provided herein, e.g., to treat, ameliorate or prevent scleroderma-associated vasculopathies and vascular changes, in particular an proliferative obliterative vasculopathy such as idiopathic obliterative vasculopathy and progressive obliterative vasculopathy, Raynaud's syndrome, edematous puffy hands, telangiectasias, digital ulcers, pulmonary arterial hypertension (PAH), myocardial dysfunction, and scleroderma renal crisis. In alternative embodiments, provided are products of manufacture and kits comprising an Adenosine Deaminase (ADA), or the polypeptide or peptide having ADA activity, including ADA conjugates, for use in treating, ameliorating or preventing: scleroderma-associated vasculopathies and vascular changes, in particular a proliferative obliterative vasculopathy such as idiopathic obliterative vasculopathy and progressive obliterative vasculopathy, Raynaud's syndrome, the edematous puffy hands, telangiectasias, digital ulcers, pulmonary arterial hypertension (PAH), myocardial dysfunction, and scleroderma renal crisis. In alternative embodiments, provided are products of manufacture and kits comprising an Adenosine Deaminase (ADA), or the polypeptide or peptide having ADA activity, including ADA conjugates, for use in preventing or decreasing the progression of scleroderma, wherein optionally the scleroderma comprises a local or focal scleroderma or a diffuse, or a systemic scleroderma.

In alternative embodiments, products of manufacture and kits as provided herein comprise instructions for practicing a method as provided herein.

The invention will be further described with reference to the examples described herein; however, it is to be understood that the invention is not limited to such examples.

EXAMPLES

Unless stated otherwise in the Examples, all recombinant DNA techniques are carried out according to standard protocols, for example, as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

Example 1: Treating or Ameliorating Scleroderma-Associated Vasculopathy and/or Preventing or Decreasing the Progression of Systemic Sclerosis (SSc)

This example describes a protocol for using a pharmaceutical composition or formulation, product of manufacture or kit as provided herein for treating, preventing or decreasing progression of Systemic Sclerosis (SSc) in a patient suffering from scleroderma-related vasculopathy. Preclinical data in animal models of systemic sclerosis have shown efficacy of adenosine deaminase when given very early after the insult; i.e., passage of time for the Fra2 mouse of eight weeks (an art accepted animal model of systemic sclerosis).

Therefore, the preclinical data demonstrates several scenarios under which patients qualify for treatment using methods as provided herein. These would include patients diagnosed with systemic sclerosis with high risk features for progression including diffuse skin involvement though some patients with limited skin involvement develop pulmonary hypertension. Thus, in alternative embodiments, patients with any signs or symptoms of pulmonary hypertension, myocarditis, inflammatory myopathy and/or arthritis, or other internal organ treatment poorly responsive to conventional symptomatic therapy qualify for treatment using methods as provided herein.

However, since the SSc-cGVHD model (an art-accepted mouse model for cGVHD) demonstrates that ADA can impact the earliest pathological expression of scleroderma, i.e., vascular changes, in alternative embodiments ADA is administered early in the earliest course of the disease, e.g., where manifestations may include Raynaud's syndrome, nonpitting edema of the hands, painful distal finger ulcers and/or facial or peri-oral skin tightening with decreased oral aperture and the particularly useful finding of abnormal capillaroscopy consistent with a sclerodermatous pattern.

In alternative embodiments, for treating patients with established scleroderma disease, including scleroderma patients with diffuse skin involvement (progressive cutaneous skin tightening, involvement of internal organs such as esophagus, lungs, heart, kidney including poorly controllable hypertension, diarrhea with malabsorption or intestinal pseudo-obstruction, dyspnea on exertion joint involvement, or scleroderma patients whose cutaneous or systemic symptoms are rapidly progressing, can be included as a group of individuals qualifying for treatment with a method as provided herein.

In alternative embodiments, another group of individuals (with early symptoms) qualifying for treatment with a method as provided herein includes those with skin involvement or abnormal capillaroscopy, puffy or swollen digits, or Raynaud's syndrome in the presence of positive tests for anti-topoisomerase 1 (anti-Scl-70) antibody, anticentromere antibody, and/or anti-RNA polymerase III antibody or a positive ANA with a nucleolar pattern.

In alternative embodiments, another group of individuals qualifying for treatment with a method as provided herein includes those having clinical signs and symptoms in the presence of skin thickening of the fingers of both hands especially with proximal involvement that strongly suggest systemic sclerosis, including ischemic fingertip ulcerations, calcinosis cutis, hyperpigmentation, mucocutaneous telangiectasia, heartburn or dysphagia of new onset, dyspnea on exertion with evidence of interstitial pulmonary changes on radiography or high resolution CT scanning or pulmonary hypertension on Doppler echocardiography.

A number of embodiments of the invention have been described. Nevertheless, it can be understood that various modifications may be made without departing from the spirit and scope of the invention. Accordingly, other embodiments are within the scope of the following claims.

What is claimed is:

1. A method for arresting, treating, ameliorating or preventing scleroderma-associated vasculopathies and vascular changes, or preventing or decreasing progression of scleroderma in an individual in need thereof, comprising:
   (a) (i) providing or having provided an Adenosine Deaminase (ADA) enzyme or a composition comprising an Adenosine Deaminase (ADA) enzyme; and
   (ii) administering or having administered an effective amount of the ADA enzyme or composition to the individual in need thereof; or
   (b) administering an effective amount of an Adenosine Deaminase (ADA) enzyme or a composition comprising an Adenosine Deaminase (ADA) enzyme to the individual in need thereof.

2. The method of claim 1, wherein the scleroderma-associated vasculopathy is a proliferative obliterative vasculopathy, wherein optionally the proliferative obliterative vasculopathy is an idiopathic obliterative vasculopathy or a progressive obliterative vasculopathy, Raynaud's syndrome, edematous puffy hands, telangiectasias, digital ulcers, pulmonary arterial hypertension (PAH), myocardial dysfunction, scleroderma renal crisis, vascular wall thickening, vascular occlusion, vascular thromboses or a destructive vasculopathy,
   wherein optionally the Raynaud's syndrome is associated with scleroderma, nonpitting edema of the hands, distal finger ulcers and/or facial or peri-oral skin tightening with decreased oral aperture, wherein the Raynaud's syndrome, nonpitting edema of the hands, distal finger ulcers and/or facial or peri-oral skin tightening are early pathological expressions of scleroderma.

3. The method of claim 1, wherein the scleroderma comprises a local or focal scleroderma or a diffuse, or a systemic scleroderma, or a focal or systemic sclerosis.

4. The method of claim 1, wherein the Adenosine Deaminase enzyme is conjugated to, linked to or covalently linked to a non-antigenic polymer, wherein optionally the non-antigenic polymer comprises a polyalkylene oxide, dextran, polyvinyl pyrrolidones, polysaccharides, starches, polyvinyl alcohols, polyacryl amides.

5. The method of claim 1, wherein the ADA enzyme is a recombinant ADA enzyme, an isolated or extracted ADA enzyme, a synthetic ADA enzyme, or a peptidomimetic version of the ADA enzyme.

6. The method of claim 5, wherein the Adenosine Deaminase enzyme is derived from an animal source, wherein optionally the animal source is a mammal, wherein optionally the mammal is a human, a bovine or a mixture thereof.

7. The method of claim 1, wherein the ADA enzyme or composition is:
   (a) manufactured as or is formulated in a polyethylene glycol conjugate form, or is administered in a polyethylene glycol conjugate form, wherein optionally the polyethylene glycol conjugate form is a PEGylated bovine adenosine deaminase enzyme, which optionally comprises: a pegademase; an elapegademase; a poly(oxy-1,2-ethanediyl), or an α-carboxy-ω-methoxy-amide, or
   (b)
   conjugated to, linked to or covalently linked to a substantially hydrolysis-resistant urethane bond between the epsilon amino groups of enzymes and a functionalized terminal group,
   wherein optionally the Adenosine Deaminase enzyme is conjugated through epsilon amino group modifications of lysines, or modifications of carboxylic acid groups.

8. The method of claim 4, wherein the ADA enzyme comprises from between about 1 to about 25 polymeric strands.

9. The method of claim 4, wherein the Adenosine Deaminase enzyme is conjugated to a polyalkylene oxide, wherein optionally the polyalkylene oxide is a polyethylene glycol (PEG),
   wherein optionally the polyalkylene oxide is a straight, branched or multi-arm polymer, and
   optionally the polyalkylene oxide or PEG has a molecular weight (MW) ranging from between about 2,000 to about 45,000 daltons.

10. The method of claim 4, wherein the Adenosine Deaminase enzyme, is conjugated with either of:

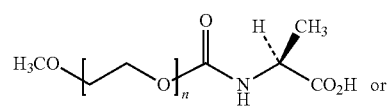

or

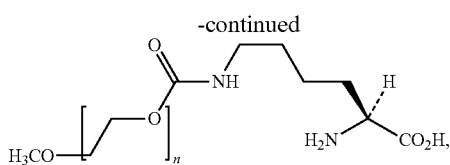

wherein n is a positive integer between 1 and about 5,000.

11. The method of claim 4, wherein the Adenosine Deaminase enzyme is a conjugate of formula:

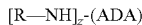

where z is a positive integer from about 1 to about 80; and R comprises a substantially non-antigenic polymer,
and optionally the substantially non-antigenic polymer is in a releasable or non-releasable form,
and optionally the substantially non-antigenic polymer is a linear, branched or a multi-armed polyalkylene oxide, wherein optionally the polyalkylene oxide is a polyethylene glycol (PEG), having average MW from between about 1000 to about 100,000 Da.

12. The method of claim 11, wherein the polyalkylene oxide is functionalized as:

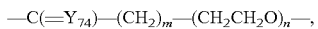

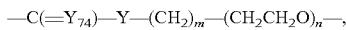

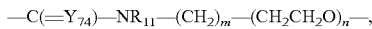

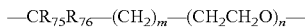

where $R_{11}$, $R_{75}$ and $R_{76}$ are independently selected from among H, $C_{1-6}$ alkyls, aryls, substituted aryls, aralkyls, heteroalkyls, substituted heteroalkyls and substituted $C_{1-6}$ alkyls; m is zero or is a positive integer; $Y_{74}$ is O or S; and n represents the degree of polymerization.

13. The method of claim 1, wherein the ADA enzyme or composition is formulated as a formulation or a pharmaceutical composition.

14. The method of claim 13, wherein the formulation or pharmaceutical composition is: formulated for enteral or parenteral administration; or, is formulated for administration by oral, nasal, rectal, intravaginal, topical, subcutaneous, intradermal, intramuscular (IM), intravenous (IV) or intrathecal (IT) intracerebral, epidural, intracranial or rectal route; or, is formulated for administration by inhalation or spray.

15. The method of claim 1, wherein the administration to the individual in need thereof is: enteral or parenteral administration; or, oral, rectal, intravaginal, topical, subcutaneous, intradermal, intramuscular (IM), intravenous (IV) or intrathecal (IT) intracerebral, epidural, intracranial or rectal, nasal, or by inhalation or spray.

16. The method of claim 13, wherein the formulation or pharmaceutical composition is contained in, or is carried in, or is in the form of:
(a) a nanoparticle, a particle, a micelle, a liposome, a lipoplex, a polymersome, a polyplex, a dendrimer, a nanolipoparticle, a vesicle or a liposomal membrane, wherein optionally the nanoparticle, particle, micelle, liposome, lipoplex, polymersome, polyplex, dendrimer, nanolipoparticle, vesicle or liposomal membrane is designed to target a specific molecule, wherein optionally the specific molecule is a biologic molecule, and optionally the nanoparticle, particle, micelle, liposome, lipoplex, polymersome, polyplex, dendrimer, nanolipoparticle, vesicle or liposomal membrane comprises a cell surface targeting compound for targeting a particular cell, wherein optionally the particular cell is a vascular cell, a fibroblast, a myocyte or heart cell or an endothelial cell, and optionally the targeting compound is a targeting polypeptide capable of specifically binding to the cell; or
(b) a tablet, a pill, a capsule, a gel, a geltab, a liquid, a powder, an emulsion, a lotion, an aerosol, a spray, a lozenge, an aqueous or a sterile or an injectable solution, or an implant.

17. The method of claim 13, wherein the effective amount of Adenosine Deaminase enzyme is:
(a) from about 0.01 to about 100 mg/kg, or from about 5 to about 50 mg/kg, or from about 10 to about 30 mg/kg, subdivided into multiple administrations from a minimum of once a day to once a year;
(b) from about 5 U/kg to about 50 U/kg, or from about 10 U/kg to about 30 U/kg, or from about 20 U/kg to about 60 U/kg, or from about 0.5 U/kg to about 5 U/kg; or a supraphysiological dose, in particular up to about 100 U/kg or more;
(c) about 250 units/m I administered weekly, optionally administered subcutaneously or IM; or
(d) any of (a) to (c), wherein the dosage is individualized based on monitoring of plasma Adenosine Deaminase enzyme, adenosine and/or other specific biomarkers after initial administrations.

18. The method of claim 13, wherein the effective amount of Adenosine Deaminase enzyme is administered in alternative dosing schedules,
wherein optionally the dosing schedules comprise:
a dosing schedule of about 10 U/kg, or between about 5 to 15 U/kg, Adagen, or about 0.067 mg/kg, or between about 0.001 to 0.12 mg/kg, EZN2279, for the first dose;
about 15 U/kg, or between about 5 to 15 U/kg, Adagen, or about 0.1 mg/kg or between about 0.05 to 0.5 mg/kg, EZN2279, for the second dose, and/or
about 30 U/kg Adagen, or between about 15 to 30 U/kg, or about 0.134 mg/kg, or between about 0.05 to 0.30 mg/kg, EZN2279 for the third dose, or a supraphysiological dose, in particular up to about 100 U/kg or more.

19. The method of claim 13, wherein an effective amount of the Adenosine Deaminase enzyme is administered any one of daily, twice a day, weekly, biweekly, monthly, or yearly.

20. The method of claim 1, wherein the ADA enzyme or composition is administered in combination with one or more of:
(a) topical nitrates or calcium channel blockers for Raynaud's syndrome, antihistamines for pruritus, H2 blockers or proton pump inhibitors for esophageal symptoms, anti-diarrheal agents or anti-spasmotics for lower GI symptoms and ADEI/ARB medications for hypertension or other renal manifestations of systemic sclerosis;
(b) immunosuppressive agents combining such agents as methotrexate, cyclophosphamide, mycophenolate mofetil, or rituximab; or
(c) antibiotics, fluids, cytokines, immunoregulatory agents, anti-inflammatory agents, complement activating agents, carbohydrate-binding domains.

* * * * *

```
                          SEQUENCE LISTING

<160> NUMBER OF SEQ ID NOS: 4

<210> SEQ ID NO 1
<211> LENGTH: 356
<212> TYPE: PRT
<213> ORGANISM: Bos taurus
<220> FEATURE:
<221> NAME/KEY: MUTAGEN
<222> LOCATION: (74)..(74)
<223> OTHER INFORMATION: Cys to Ser mutein

<400> SEQUENCE: 1

Ala Gln Thr Pro Ala Phe Asn Lys Pro Lys Val Glu Leu His Val His
1               5                   10                  15

Leu Asp Gly Ala Ile Lys Pro Glu Thr Ile Leu Tyr Tyr Gly Arg Lys
                20                  25                  30

Arg Gly Ile Ala Leu Pro Ala Asp Thr Pro Glu Glu Leu Gln Asn Ile
            35                  40                  45

Ile Gly Met Asp Lys Pro Leu Ser Leu Pro Glu Phe Leu Ala Lys Phe
50                  55                  60

Asp Tyr Tyr Met Pro Ala Ile Ala Gly Ser Arg Glu Ala Val Lys Arg
65                  70                  75                  80

Ile Ala Tyr Glu Phe Val Glu Met Lys Ala Lys Asp Gly Val Val Tyr
                85                  90                  95

Val Glu Val Arg Tyr Ser Pro His Leu Leu Ala Asn Ser Lys Val Glu
                100                 105                 110

Pro Ile Pro Trp Asn Gln Ala Gly Asp Leu Thr Pro Asp Glu Val
            115                 120                 125

Val Ser Leu Val Asn Gln Gly Leu Gln Glu Gly Glu Arg Asp Phe Gly
            130                 135                 140

Val Lys Val Arg Ser Ile Leu Cys Cys Met Arg His Gln Pro Ser Trp
145                 150                 155                 160

Ser Ser Glu Val Val Glu Leu Cys Lys Lys Tyr Arg Glu Gln Thr Val
                165                 170                 175

Val Ala Ile Asp Leu Ala Gly Asp Glu Thr Ile Glu Gly Ser Ser Leu
            180                 185                 190

Phe Pro Gly His Val Lys Ala Tyr Ala Glu Ala Val Lys Ser Gly Val
            195                 200                 205

His Arg Thr Val His Ala Gly Glu Val Gly Ser Ala Asn Val Val Lys
            210                 215                 220

Glu Ala Val Asp Thr Leu Lys Thr Glu Arg Leu Gly His Gly Tyr His
225                 230                 235                 240

Thr Leu Glu Asp Thr Thr Leu Tyr Asn Arg Leu Arg Gln Glu Asn Met
                245                 250                 255

His Phe Glu Val Cys Pro Trp Ser Ser Tyr Leu Thr Gly Ala Trp Lys
            260                 265                 270

Pro Asp Thr Glu His Pro Val Val Arg Phe Lys Asn Asp Gln Val Asn
            275                 280                 285

Tyr Ser Leu Asn Thr Asp Asp Pro Leu Ile Phe Lys Ser Thr Leu Asp
            290                 295                 300

Thr Asp Tyr Gln Met Thr Lys Asn Glu Met Gly Phe Thr Glu Glu Glu
305                 310                 315                 320
```

```
Phe Lys Arg Leu Asn Ile Asn Ala Ala Lys Ser Ser Phe Leu Pro Glu
                325                 330                 335

Asp Glu Lys Lys Glu Leu Leu Asp Leu Leu Tyr Lys Ala Tyr Gly Met
            340                 345                 350

Pro Ser Pro Ala
        355

<210> SEQ ID NO 2
<211> LENGTH: 1074
<212> TYPE: DNA
<213> ORGANISM: Bos taurus

<400> SEQUENCE: 2
atggctcaga ccccggcttt caacaaaccg aaggtagaaa ctgcacgtac acctggatggt      60 gctatcaaac cggagactat cctgtactat ggtcgtaagc gtggcatcgc tctgccggct     120
gacactccgg aagaactgca gaacatcatc ggcatggaca aaccgctgtc tctgccggaa     180
ttcctggcta aattcgacta ctacatgccg gctatcgctg gttctcgtga agcagtcaaa     240
cgtatcgctt acgaattcgt agaaatgaaa gctaaagatg gtgtagtata cgttgaagtt     300
cgttactctc gcacctgct  ggcaaactct aaagttgaac cgatcccgtg aaccaggca      360 gaaggcgatc tgactccgga tgaagtagtt tctctggtta ccagggtct gcaggagggt      420 gaacgcgatt tcggcgtaaa agttcgttct atcctgtgct gcatgcgcca ccagccgtct     480
tggtcttctg aagttgttga actgtgcaag aaataccgtg agcagaccgt agttgctatc     540
gatctggcag gtgatgaaac catcgaaggt tcttctctgt tccgggtca cgtaaaggct      600 tatgctgaag ctgttaaatc tggcgtacac cgtactgtac acgcaggtga agttggttct     660
gctaacgttg ttaaagaagc tgttgacacc ctgaaaactg aacgcctggg tcacggctac     720 cacacctgg  aagacaccac cctgtacaac cgtctgcgtc aggaaaacat gcacttcgaa     780
gtttgtccgt ggtcctctta cctgactggt gcttggaaac cggacaccga cacccggtt     840 gttcgtttca aaacgacca  ggtaaactac tctctgaaca ctgacgatcc gctgatcttc     900
aaatctaccc tggacaccga ctaccagatg accaaaaacg aaatgggttt cactgaagaa     960
gaattcaaac gtctgaacat caacgctgct aagtcctctt ttctgccgga agatgagaaa    1020
aaagaactgc tggaccctgct gtacaaggca tacggtatgc cgtctccggc ttaa         1074

<210> SEQ ID NO 3
<211> LENGTH: 362
<212> TYPE: PRT
<213> ORGANISM: Homo sapiens
<220> FEATURE:
<221> NAME/KEY: MUTAGEN
<222> LOCATION: (74)..(74)
<223> OTHER INFORMATION: Cys to Ser mutein

<400> SEQUENCE: 3

Ala Gln Thr Pro Ala Phe Asp Lys Pro Lys Val Glu Leu His Val His
1               5                   10                  15

Leu Asp Gly Ser Ile Lys Pro Glu Thr Ile Leu Tyr Tyr Gly Arg Arg
            20                  25                  30

Arg Gly Ile Ala Leu Pro Ala Asn Thr Ala Glu Gly Leu Leu Asn Val
        35                  40                  45

Ile Gly Met Asp Lys Pro Leu Thr Leu Pro Asp Phe Leu Ala Lys Phe
    50                  55                  60

Asp Tyr Tyr Met Pro Ala Ile Ala Gly Ser Arg Glu Ala Ile Lys Arg
```

```
                65                  70                  75                  80
Ile Ala Tyr Glu Phe Val Glu Met Lys Ala Lys Glu Gly Val Val Tyr
                    85                  90                  95

Val Glu Val Arg Tyr Ser Pro His Leu Leu Ala Asn Ser Lys Val Glu
                    100                 105                 110

Pro Ile Pro Trp Asn Gln Ala Glu Gly Asp Leu Thr Pro Asp Glu Val
                    115                 120                 125

Val Ala Leu Val Gly Gln Gly Leu Gln Glu Gly Glu Arg Asp Phe Gly
                    130                 135                 140

Val Lys Ala Arg Ser Ile Leu Cys Cys Met Arg His Gln Pro Asn Trp
145                 150                 155                 160

Ser Pro Lys Val Val Glu Leu Cys Lys Lys Tyr Gln Gln Thr Val
                    165                 170                 175

Val Ala Ile Asp Leu Ala Gly Asp Glu Thr Ile Pro Gly Ser Ser Leu
                    180                 185                 190

Leu Pro Gly His Val Gln Ala Tyr Gln Glu Ala Val Lys Ser Gly Ile
                    195                 200                 205

His Arg Thr Val His Ala Gly Glu Val Gly Ser Ala Glu Val Val Lys
                    210                 215                 220

Glu Ala Val Asp Ile Leu Lys Thr Glu Arg Leu Gly His Gly Tyr His
225                 230                 235                 240

Thr Leu Glu Asp Gln Ala Leu Tyr Asn Arg Leu Arg Gln Glu Asn Met
                    245                 250                 255

His Phe Glu Ile Cys Pro Trp Ser Ser Tyr Leu Thr Gly Ala Trp Lys
                    260                 265                 270

Pro Asp Thr Glu His Ala Val Ile Arg Leu Lys Asn Asp Gln Ala Asn
                    275                 280                 285

Tyr Ser Leu Asn Thr Asp Asp Pro Leu Ile Phe Lys Ser Thr Leu Asp
                    290                 295                 300

Thr Asp Tyr Gln Met Thr Lys Arg Asp Met Gly Phe Thr Glu Glu Glu
305                 310                 315                 320

Phe Lys Arg Leu Asn Ile Asn Ala Ala Lys Ser Ser Phe Leu Pro Glu
                    325                 330                 335

Asp Glu Lys Arg Glu Leu Leu Asp Leu Leu Tyr Lys Ala Tyr Gly Met
                    340                 345                 350

Pro Pro Ser Ala Ser Ala Gly Gln Asn Leu
                    355                 360

<210> SEQ ID NO 4
<211> LENGTH: 1089
<212> TYPE: DNA
<213> ORGANISM: Homo sapiens

<400> SEQUENCE: 4
atggctcaga cacccgcatt tgataaaccg aaagtggaac tgcatgtcca cctggatggt      60
agcatcaaac cggaaactat cttatattac ggtcggcgtc gtggtattgc gttgccggca     120
aacacggctg aaggtttgct gaacgtgatc ggcatggaca aaccgctgac cttgccggat     180
tttttggcga aatttgatta ttatatgccg gcgattgctg ttcccgcga ggcaatcaaa     240 cgcatcgcgt atgagtttgt tgaaatgaaa gcgaaagaag gcgttgtgta tgttgaggtc     300
cgttacagtc cgcatctgct ggctaacagc aaggtagaac ctatcccctg gaaccaagct     360
gaaggcgatc tgacgccgga tgaagtggtt gctctggtgg gtcagggttt acaggagggg     420
gagcgcgatt ttggcgttaa agctcgctct attttatgtt gcatgcgcca tcagcccaat     480
```

```
tggtccccga aagtggttga actttgtaaa aagtaccaac aacagaccgt tgtcgcgatt      540
gatttggcag gcgatgaaac aattccaggc agctccctgt tgccagggca cgtgcaagcg      600
taccaagaag cagtgaaaag cggcatccac cggactgtcc acgccggcga ggtcggtagc      660
gccgaggttg tgaaagaagc cgtggacatc ctgaaaaccg agcggctggg ccatgggtac      720
cacacactgg aggatcaggc attatataac cgcttacgcc aggaaaatat gcatttcgaa      780
atttgtccgt ggagtagtta cttaactggc gcgtggaaac cggataccga acatgcggtt      840
atccgcttaa agaatgatca agcaaattac agtctgaata cagatgatcc cctgattttc      900
aagtctaccc tggacacaga ttatcagatg acgaagcggg atatgggatt tacggaagaa      960
gaatttaagc gtctcaatat caatgcggcg aaatcttcat ttctgccgga agatgagaaa     1020
cgtgagttgc tggatcttct gtacaaggcc tacggtatgc cgccgagcgc atcggccggg     1080
cagaacctg                                                             1089
```